United States Patent
Hindrichs et al.

(10) Patent No.: US 7,361,181 B2
(45) Date of Patent: Apr. 22, 2008

(54) APPARATUS AND METHODS FOR CREATING ANASTOMOSES

(75) Inventors: Paul J Hindrichs, Plymouth, MN (US); Michael P Brenzel, St. Paul, MN (US); Richard G Cornelius, Wayzata, MN (US); William J Swanson, St. Paul, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 748 days.

(21) Appl. No.: 10/678,405

(22) Filed: Oct. 3, 2003

(65) Prior Publication Data

US 2004/0068279 A1 Apr. 8, 2004

Related U.S. Application Data

(60) Provisional application No. 60/416,500, filed on Oct. 4, 2002.

(51) Int. Cl.
*A61B 17/11* (2006.01)
*A61B 1/32* (2006.01)

(52) U.S. Cl. ........................................ 606/153; 600/201
(58) Field of Classification Search ...................... None
See application file for complete search history.

(56) References Cited

U.S. PATENT DOCUMENTS

| 5,411,510 | A | * | 5/1995 | Fugo | 606/166 |
| 5,628,760 | A | * | 5/1997 | Knoepfler | 606/170 |
| 5,976,178 | A | | 11/1999 | Goldsteen et al. | 623/1 |
| 6,001,116 | A | * | 12/1999 | Heisler et al. | 606/180 |
| 6,063,114 | A | * | 5/2000 | Nash et al. | 623/1.36 |
| 6,113,612 | A | * | 9/2000 | Swanson et al. | 623/1.15 |
| 6,113,616 | A | * | 9/2000 | Taylor et al. | 606/167 |
| 6,152,937 | A | | 11/2000 | Peterson et al. | 606/153 |
| 6,287,322 | B1 | * | 9/2001 | Zhu et al. | 606/213 |
| 6,428,550 | B1 | | 8/2002 | Vargas et al. | 606/153 |
| 6,602,263 | B1 | | 8/2003 | Swanson et al. | 606/153 |
| 6,699,256 | B1 | | 3/2004 | Logan et al. | 606/153 |
| 2002/0169466 | A1 | | 11/2002 | Peterson et al. | 606/153 |
| 2002/0183769 | A1 | | 12/2002 | Swanson et al. | 606/153 |

FOREIGN PATENT DOCUMENTS

WO    WO 01/39672    6/2001

\* cited by examiner

*Primary Examiner*—Glenn K. Dawson
(74) *Attorney, Agent, or Firm*—Fish & Neave IP Group, Ropes & Gray LLP; Jeffrey C. Aldridge

(57) ABSTRACT

Apparatus and methods for creating anastomoses are provided. An incision tool for creating an incision having a controlled length in a side wall of a patient's body tissue conduit is provided. A delivery device for inserting a hollow annular connector into an incision in a side wall of a patient's body tissue conduit is provided. The delivery device may include first and second anvil structures around which the connector may be disposed. By moving the first anvil structure away from the second anvil structure, the connector may expand to a desired configuration (e.g., non-round) within the aperture. In one example, the connector may be inserted into the aperture to hold the aperture open prior to attachment of a graft conduit to the aperture, thereby allowing a physician to inspect the aperture and the surrounding tissue.

13 Claims, 32 Drawing Sheets

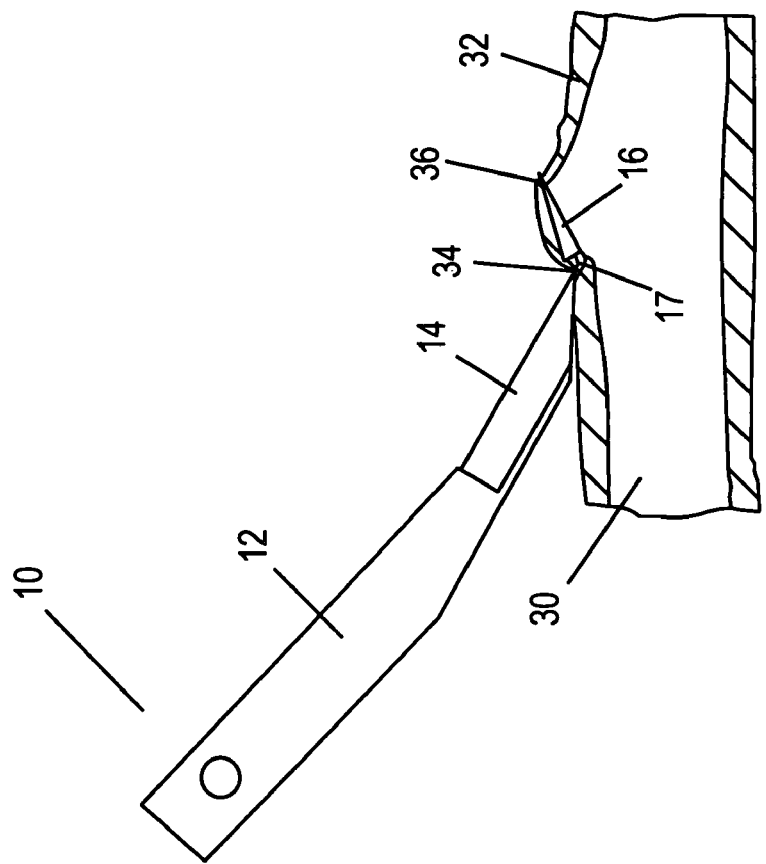
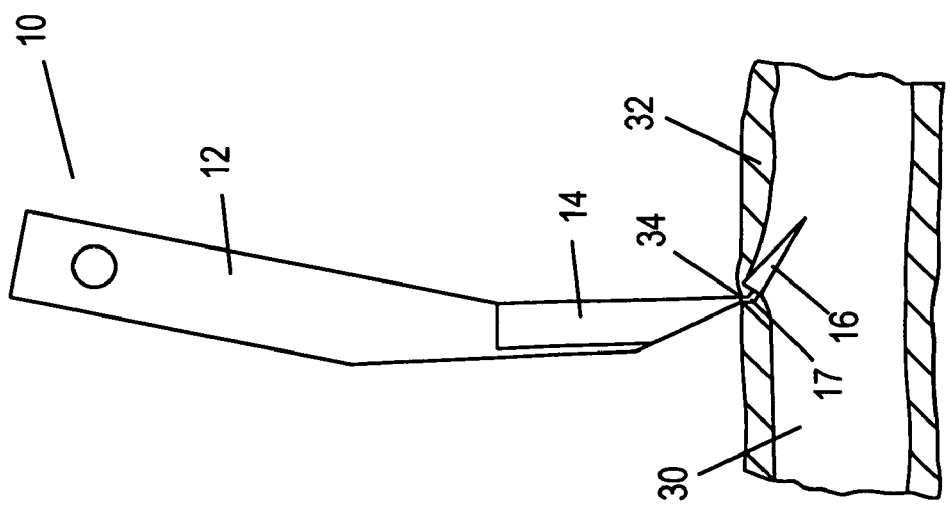

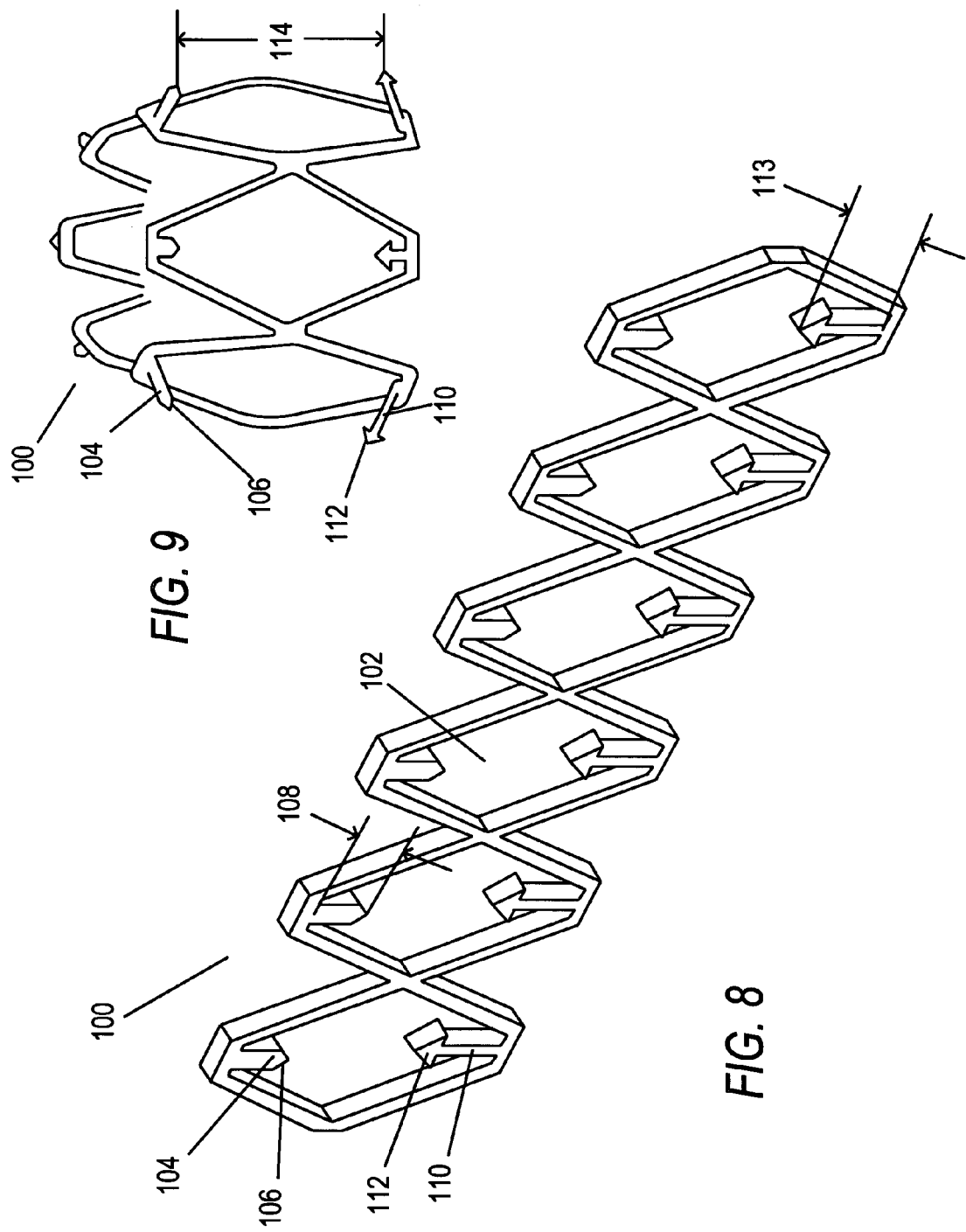

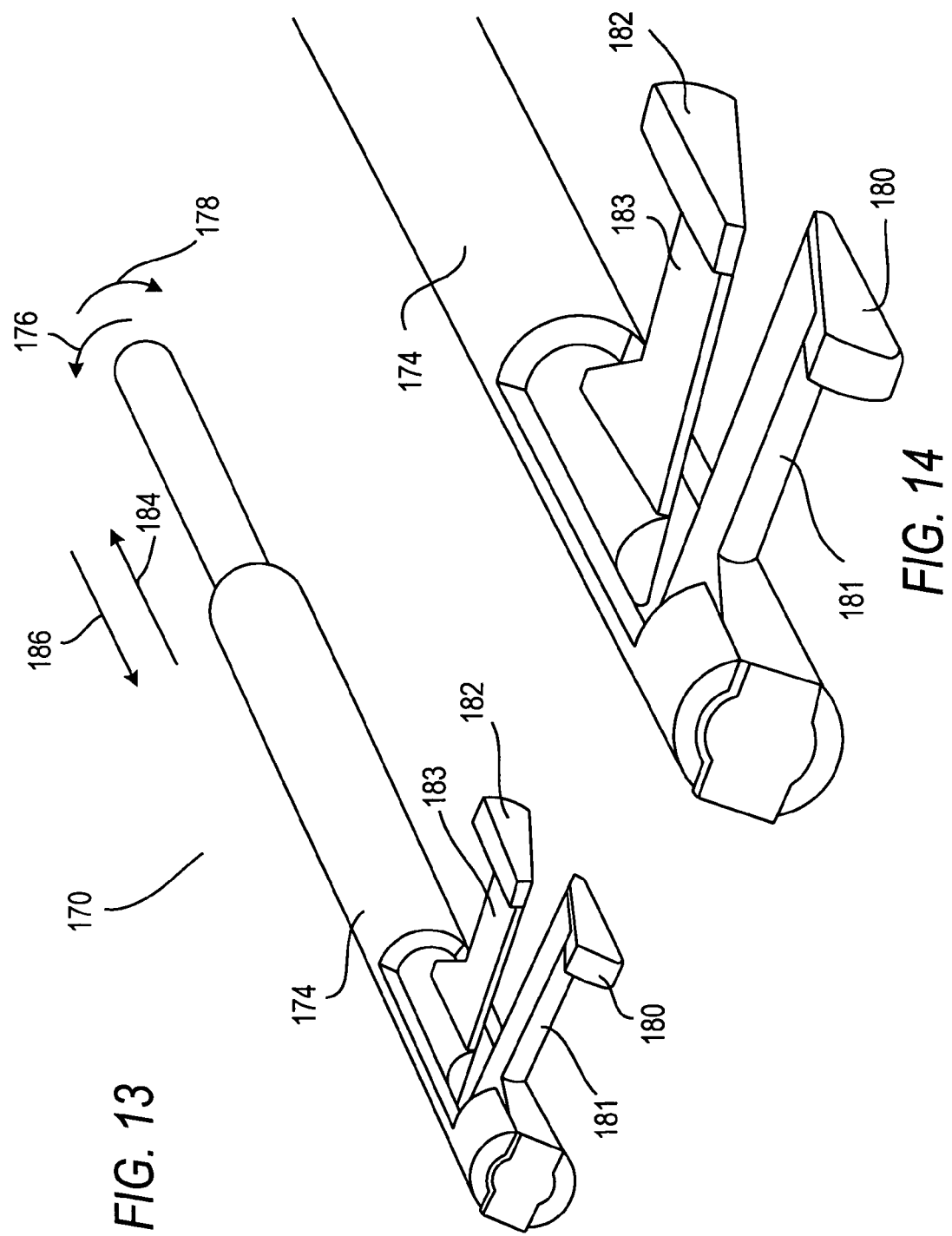

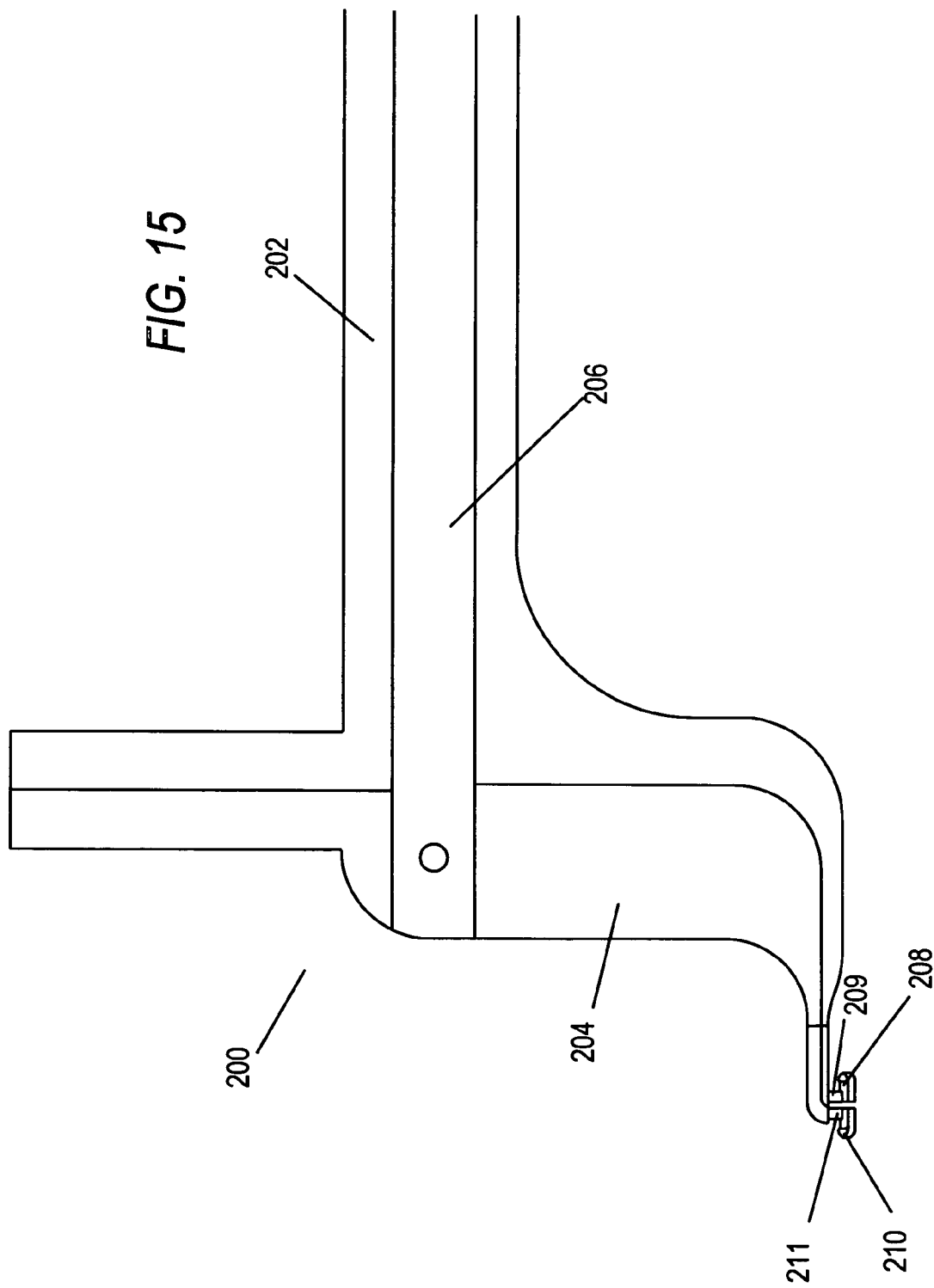

APPARATUS AND METHODS FOR CREATING ANASTOMOSES

This application claims the benefit of U.S. provisional patent application No. 60/416,500, filed Oct. 4, 2002, which is hereby incorporated by reference herein in its entirety.

BACKGROUND OF THE INVENTION

This invention relates to apparatus and methods for creating anastomoses and, more particularly, to apparatus and methods for creating anastomoses to small diameter body fluid conduits in a patient.

There are many medical procedures in which it is necessary to make anastomotic connections between tubular body fluid conduits in a patient. An anastomotic connection (or anastomosis) is a connection which allows body fluid flow between the lumen of the two conduits that are connected, preferably without allowing body fluid to leak out of the conduits at the location of the connection. As just one example of a procedure in which an anastomosis is needed, in order to bypass an obstruction in a patient's coronary artery, a tubular graft supplied with aortic blood may be connected via an anastomosis to the coronary artery (i.e., the target vessel) downstream from the obstruction. The anastomosis may be between the end of the graft and an aperture in the side wall of the coronary artery (a so-called end-to-side anastomosis), or the anastomosis may be between an aperture in the side wall of the graft and an aperture in the side wall of the coronary artery (a so-called side-to-side anastomosis).

The graft may be natural conduit, synthetic conduit, or a combination of natural and synthetic conduits. If natural conduit is used, it may be wholly or partly relocated from elsewhere in the patient (e.g., wholly relocated saphenous vein graft ("SVG") or partly relocated internal mammary artery ("IMA")). Alternatively, no relocation of the graft may be needed (e.g., a length of vein on the heart becomes a "graft" around an obstruction in an immediately adjacent coronary artery).

More than one anastomosis may be needed. For example, a second anastomosis may be needed between an upstream portion of the graft conduit and the aorta or the coronary artery upstream from the obstruction in that artery. Again, this second anastomosis may be either an end-to-side anastomosis or a side-to-side anastomosis. Alternatively, no second upstream anastomosis may be required at all (e.g., if the graft is an only-partly-relocated IMA).

Prior to creating an anastomosis between a graft conduit and a target vessel, an incision may be made in the target vessel. This incision typically ranges in size from about 2 mm to about 6 mm for small-bore vessels. The most common technique of making this incision is by using a scalpel to make a small incision in the target vessel, and then elongating the small incision using Potts scissors. This technique results in an incision having some estimated length, rather than a controlled, fixed length.

A common technique for making an anastomosis is manually suturing two tubular body fluid conduits together around an opening between them. Manual suturing is difficult and time-consuming, and the quality of the anastomosis that results is highly dependent on the skill of the person doing the suturing. Various types of mechanical connectors have been developed to reduce or eliminate the need for suturing, but improvements are constantly sought for such mechanical connectors with respect to considerations such as ease and speed of use, ease of manufacture, strength and permanence of the resulting connection, etc.

Accordingly, it would be desirable to provide apparatus and methods for creating anastomoses between tubular body fluid conduits in a patient.

SUMMARY OF THE INVENTION

In accordance with the present invention, apparatus and methods for creating anastomoses to small diameter vessels in a patient are provided. The present invention may involve both a one-connector system and a two-connector system. One or both of these connector systems may be non-round connector systems. In other words, the anastomotic connection resulting from either of the one-connector system or the two-connector system may be non-round (e.g., oval). In a small diameter vessel, the creation of a non-round anastomotic connection may, for example, prevent occlusion of the small diameter vessel caused by the healing response of the tissue at the site of the anastomosis.

The one-connector system of the present invention engages tissue and creates a seal similarly to, for example, the connectors described in Swanson U.S. Pat. No. 6,602,263, which is hereby incorporated by reference herein in its entirety. The one-connector system improves upon both making an incision in a target vessel and expanding the connector in the axial and radial directions.

The two-connector system of the present invention allows a user (e.g., a physician) to create a connection in more controlled steps, and provides a new alternative coupling between first and second vessels. (It should be noted that the terms "vessel," "body fluid conduit," "body tissue conduit," and "conduit" are used interchangeably herein.) The two-connector system may include two plastically deformable connectors. Although many of the examples provided hereinbelow are described in relation to the two-connector system, it should be noted that the apparatus and methods of the present invention are also applicable to the one-connector system.

In some embodiments of the present invention, apparatus for creating an incision having a controlled length in a side wall of a patient's body tissue conduit may be provided. The apparatus may include a tip portion having a sharpened free end portion that is configured for insertion into the side wall of the body tissue conduit such that the sharpened free end portion creates a first hole in the side wall and a second hole in the side wall at some distance from the first hole. The apparatus may include a blade portion attached to the tip portion that is configured to create an incision between the first and second holes. An angle between the blade portion and the tip portion may be less than 180°.

In some embodiments of the present invention, a method for creating an incision having a controlled length in a side wall of a patient's body tissue conduit may be provided. An incision tool may be provided that includes a tip portion having a sharpened free end portion and a blade portion attached to the tip portion. An angle between the blade portion and the tip portion may be less than 180°. First and second holes may be created in the side wall of the body tissue conduit with the sharpened free end portion. A cut may be made from the first hole to the second hole with the blade portion such that an incision is created.

In some embodiments of the present invention, apparatus for inserting a hollow annular connector into an aperture in a side wall of a body tissue conduit may be provided. The apparatus may include A first anvil structure that is attached to a first movable member such that the first movable member effects the movement of the first anvil structure. The apparatus may include a second anvil structure. The first and second anvil structures may be configured for disposition at least partially within the hollow annular connector.

In some embodiments of the present invention, a method for inserting a hollow annular connector into an aperture in a side wall of a patient's body tissue conduit may be provided. A delivery device may be provided that includes a first anvil structure that is attached to a first movable member such that the first movable member effects the movement of the first anvil structure. The delivery device may include a second anvil structure. The first and second anvil structures may be disposed at least partially within the hollow annular connector. The hollow annular connector may be introduced into the aperture. The first anvil structure may be advanced away from the second anvil structure along the axis of the body tissue conduit such that the connector expands in the axial direction of the body tissue conduit. The first anvil structure may be advanced away from the second anvil structure perpendicular to the axis of the body tissue conduit such that the connector expands in the radial direction of the body tissue conduit.

In some embodiments of the present invention, apparatus for inserting a hollow annular connector into an aperture in a side wall of a body tissue conduit may be provided. The apparatus may include an expansion structure and a movable member attached to the expansion structure that effects the movement of the expansion structure. The movement of the expansion structure may be configured to expand the connector in the axial direction of the body tissue conduit and in the radial direction of the body tissue conduit.

In some embodiments of the present invention, apparatus for holding open an incision in a patient's body tissue conduit may be provided. The apparatus may include first and second incision members and first and second end portions. The first end portion may be attached to the first incision member, and the second end portion may be attached to the second incision member. The first and second incision members may be configured for insertion into the incision by compressing the first and second end portions.

In some embodiments of the present invention, apparatus for producing a hollow annular anastomotic connection between a first aperture in a side wall of a patient's body tissue conduit and a second aperture in a side wall of a graft conduit are provided. The apparatus may include a first hollow annular connector that is configured for installation in the first aperture in the side wall of the body tissue conduit. The apparatus may include a second hollow annular connector that is configured for disposition annularly within the second aperture in the side wall of the graft conduit, and that is configured for attachment to the body tissue conduit such that the first connector is encapsulated by the second connector.

Further features of the invention, its nature and various advantages will be more apparent from the accompanying drawings and the following detailed description.

BRIEF DESCRIPTION OF THE DRAWINGS

FIG. 2 is a sectional view illustrating a stage of a procedure involving the tool of FIG. 1 in accordance with the present invention.

FIG. 3 is a view similar to FIG. 2 illustrating a further stage of a procedure in accordance with the present invention.

FIG. 8 is a planar development of a target vessel connector structure in accordance with the present invention.

FIG. 9 is a perspective view of the connector structure which is shown in planar development in FIG. 8 in accordance with the present invention.

FIG. 13 is a perspective view of a delivery device in accordance with the present invention.

FIG. 14 is another perspective view of the delivery device of FIG. 13 in accordance with the present invention.

FIG. 15 is a perspective view of another delivery device in accordance with the present invention.

Figure 30:
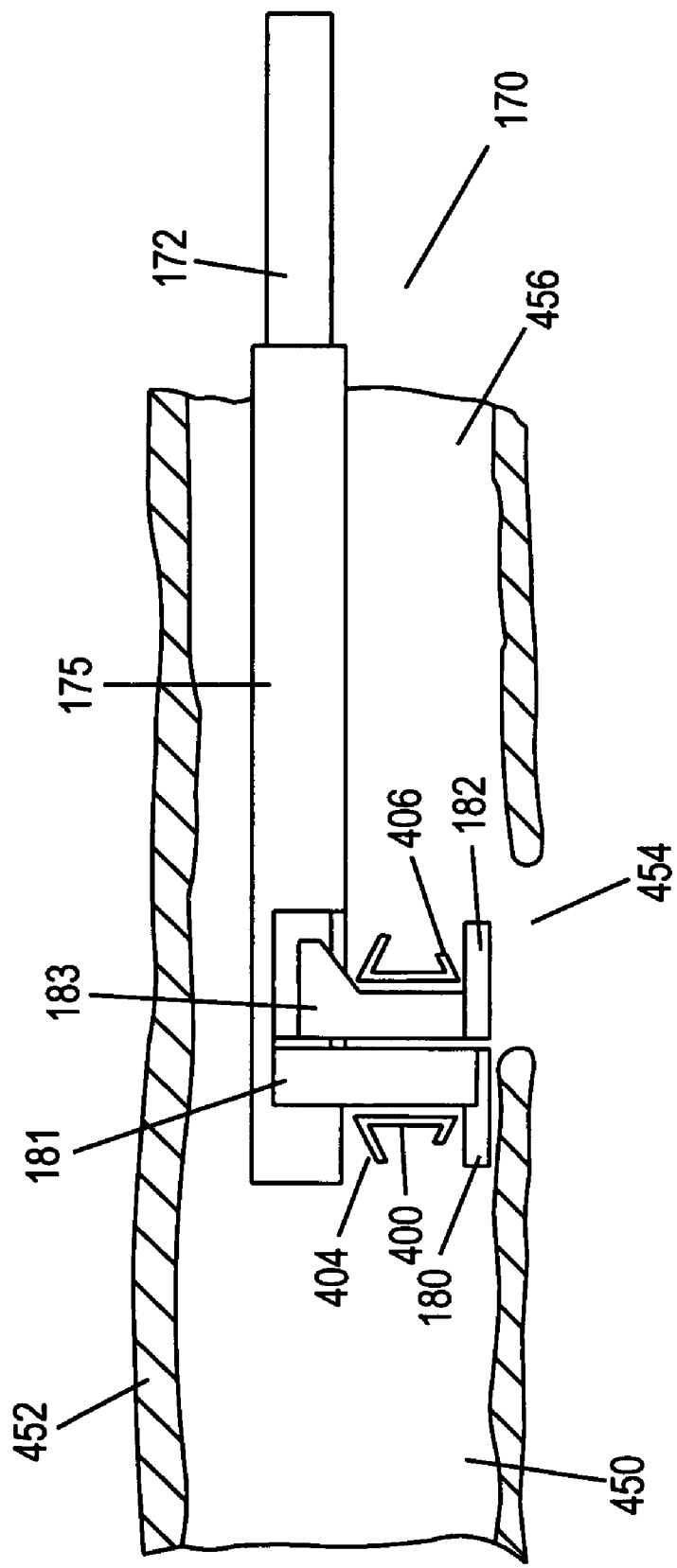
FIG. 30 is a sectional view illustrating a stage of a procedure involving the delivery device of FIGS. 13 and 14 and a simplified version of the graft connector structure of FIG. 28 in accordance with the present invention.
Figure 31:
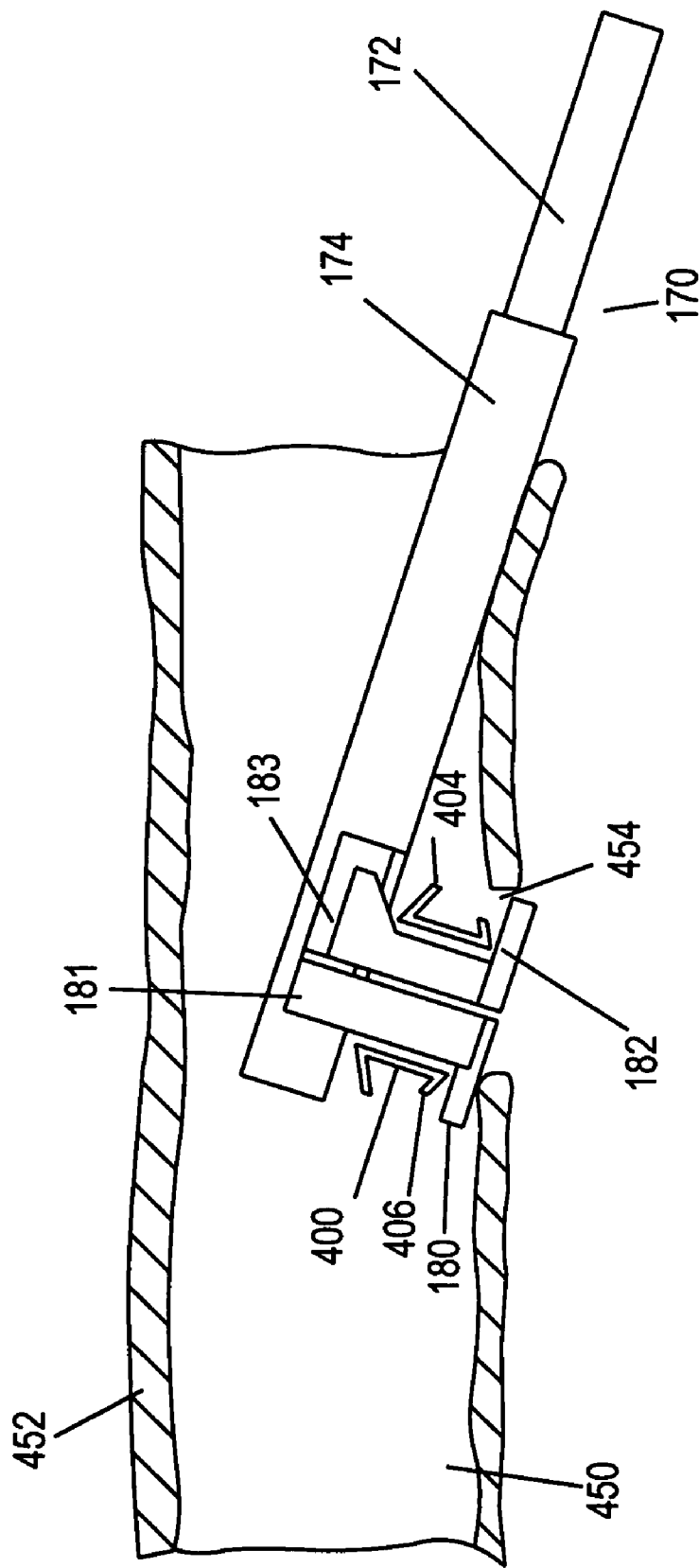

FIG. 31 is a view similar to FIG. 30 illustrating a further stage of a procedure in accordance with the present invention.

Figure 32:
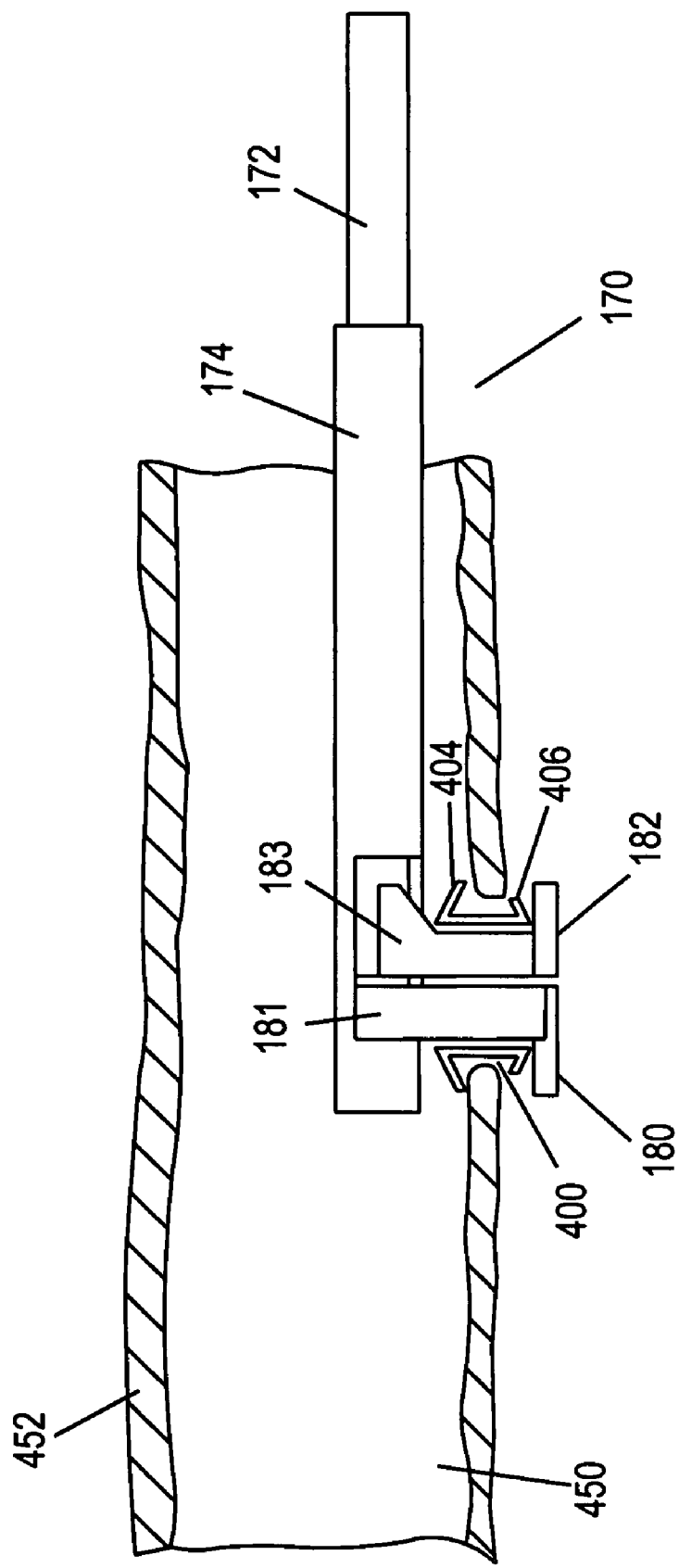

FIG. 32 is a view similar to FIG. 31 illustrating a later stage of a procedure in accordance with the present invention.

Figure 33:
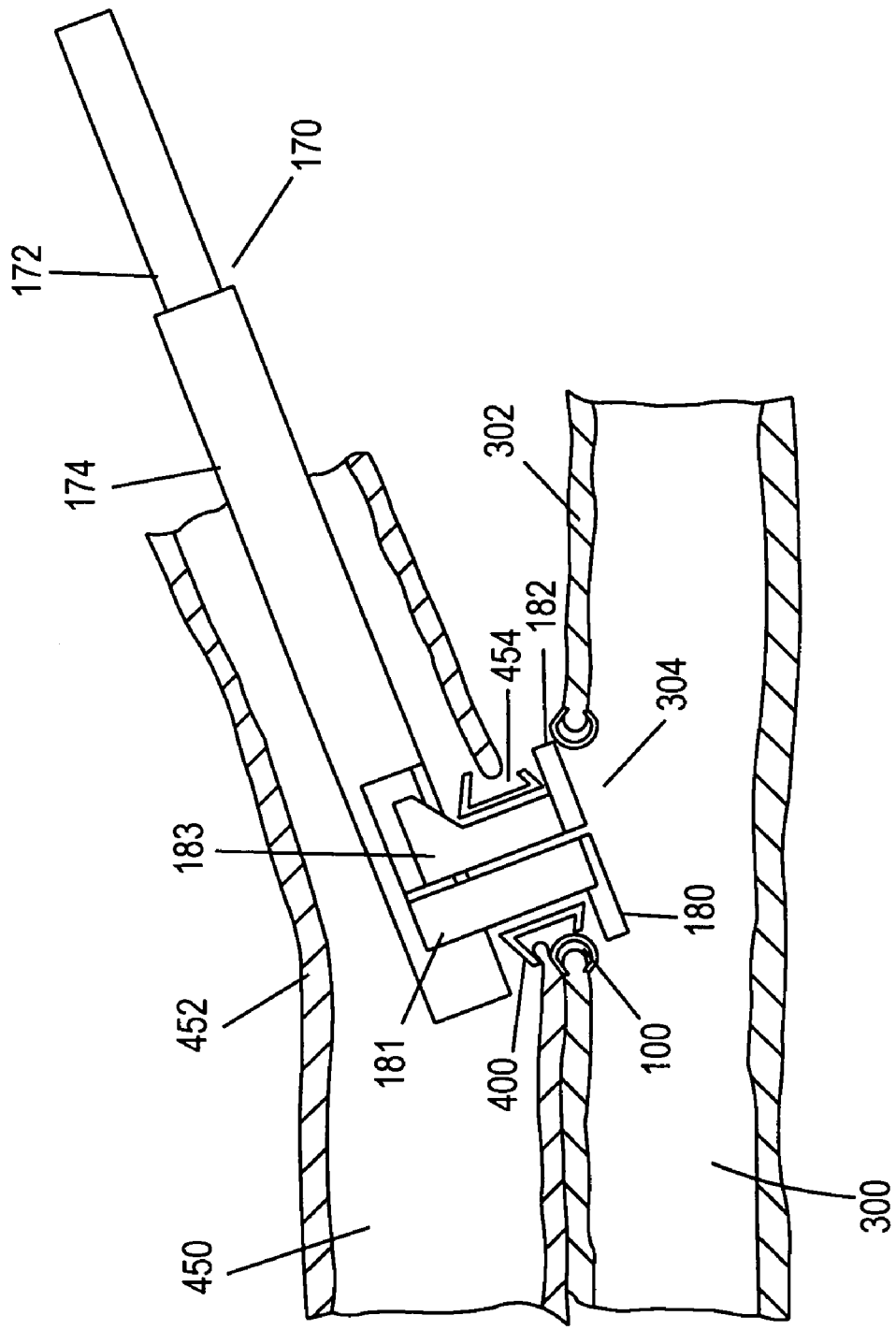

FIG. 33 is a view similar to FIG. 32 illustrating a still later stage of a procedure in accordance with the present invention.

Figure 34:
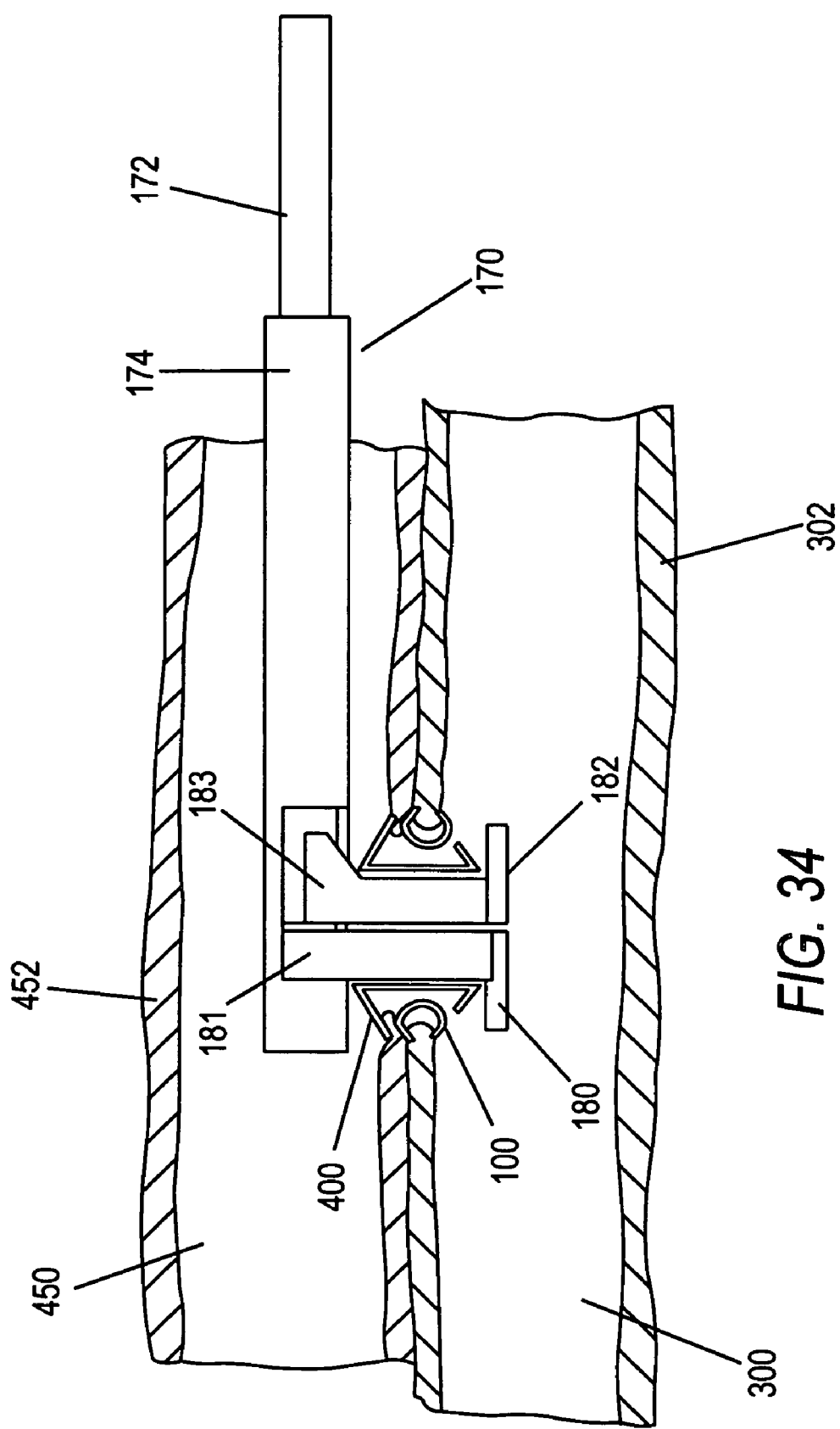

FIG. 34 is a view similar to FIG. 33 illustrating a later stage of a procedure in accordance with the present invention.

Figure 35:
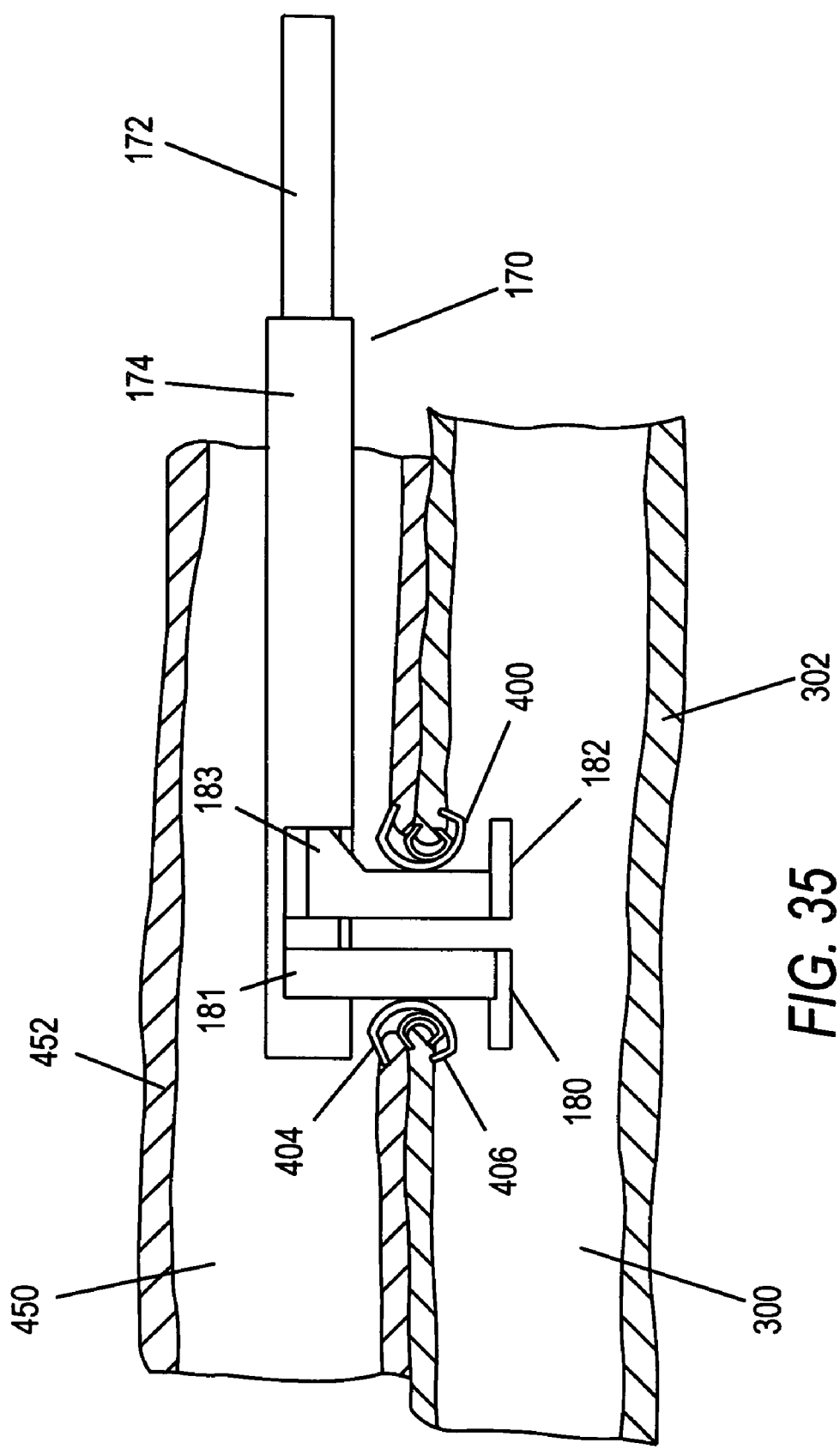

FIG. 35 is a view similar to FIG. 34 illustrating a still later stage of a procedure in accordance with the present invention.

Figure 36:
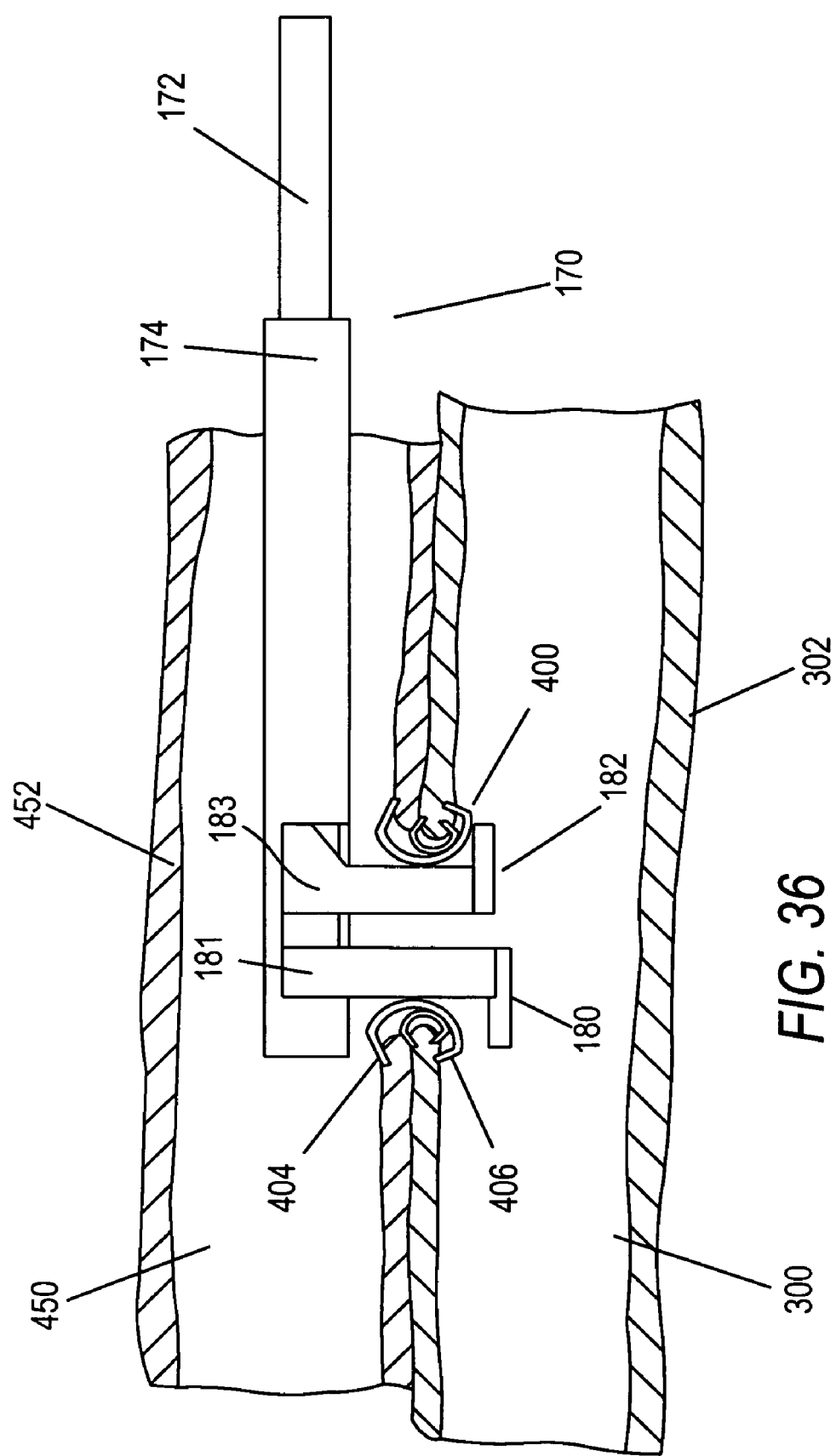

FIG. 36 is a view similar to FIG. 35 illustrating a further stage of a procedure in accordance with the present invention.

Figure 37:
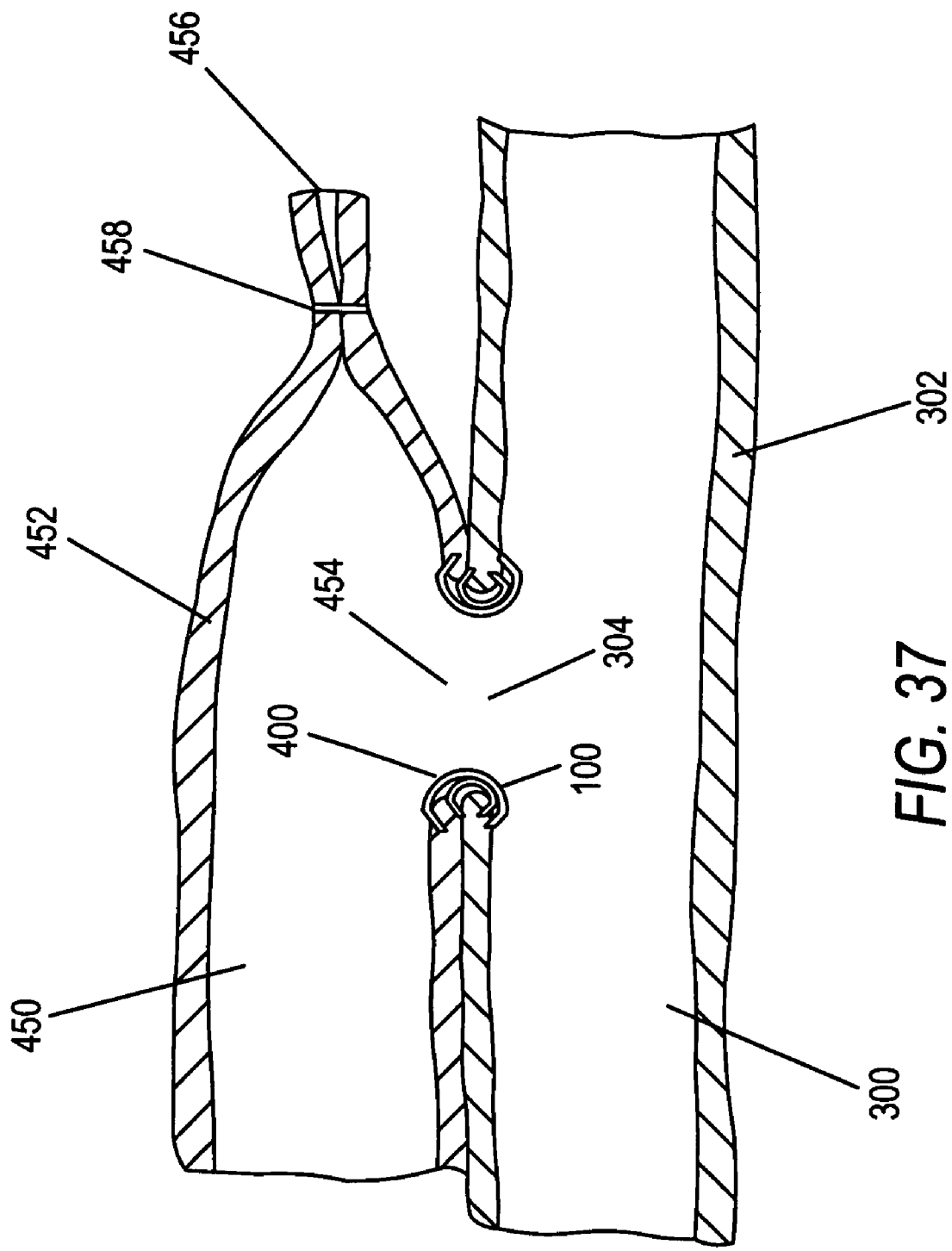

FIG. 37 is a view similar to FIG. 36 illustrating a later stage of a procedure in accordance with the present invention.

Figure 38:
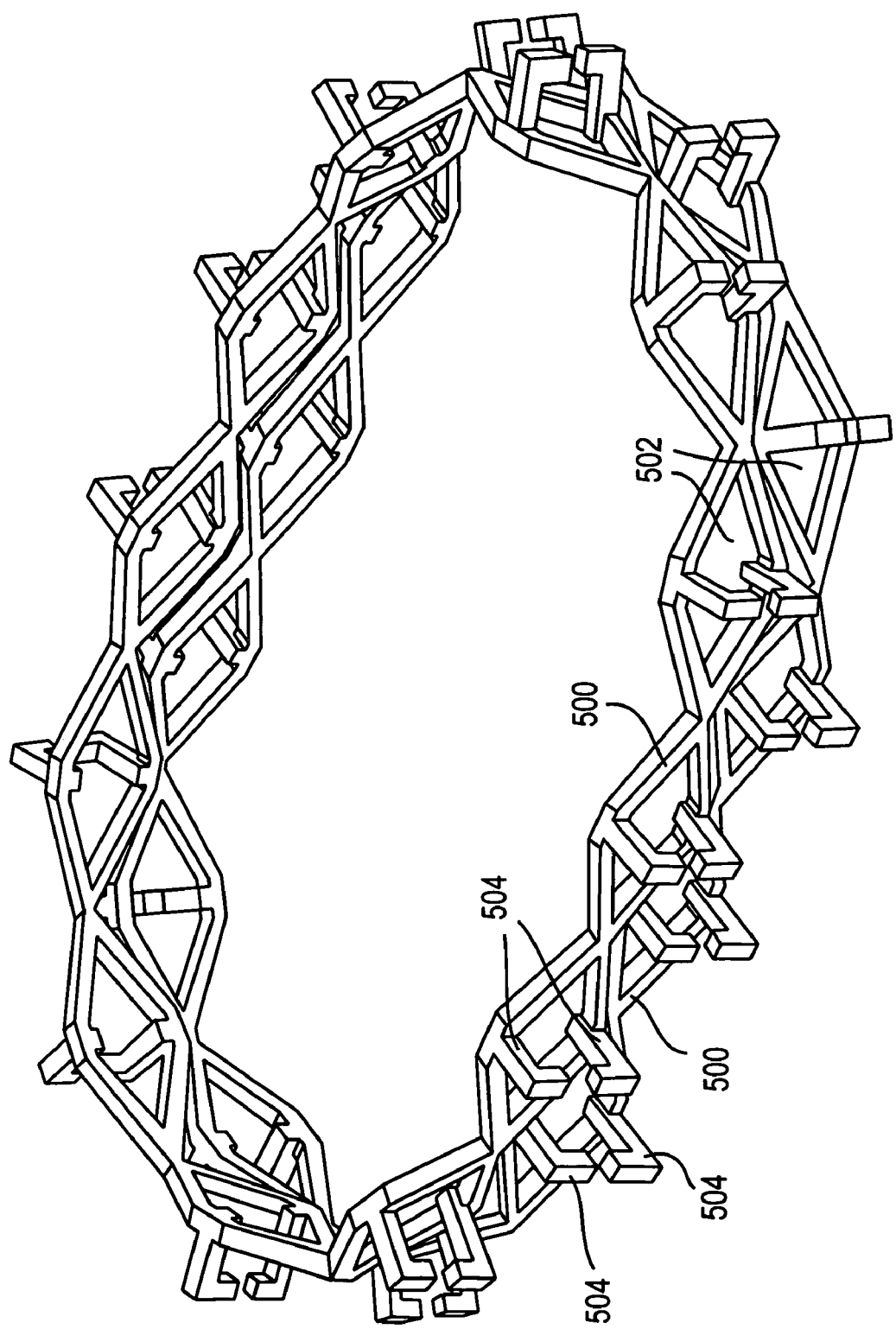

FIG. 38 is a perspective view of an alternative connector assembly in accordance with the present invention.

DETAILED DESCRIPTION OF THE INVENTION

In accordance with the present invention, apparatus and methods for creating anastomoses to small diameter vessels in a patient are provided.

In some embodiments of the present invention, an incision having a controlled, predetermined length may be made in one or both of a target vessel and a graft conduit prior to creating an anastomosis between the target vessel and the graft conduit. (It should be noted that, although apparatus and methods for making a controlled-length incision will be described herein in relation to vessels between which an anastomosis is to be created, the controlled-length incision may be made in any tubular body fluid conduit in a patient.) Apparatus and methods for making a controlled length incision are also described, for example, in concurrently-filed, commonly-assigned U.S. patent application Ser. No. 10/678,403, filed Oct 3, 2003, which is hereby incorporated by reference herein in its entirety.

The vessel incision tool of the present invention may be used in a manner similar to that of a suture needle. The vessel incision tool includes a sharp tip for insertion into the side wall of a vessel. By inserting the tip into the side wall of the vessel, a first small hole is created in the side wall. The tool may include a small recess that provides a physician with tactile and visual feedback when the tip has been inserted far enough into the vessel. The vessel incision tool may be rotated upwards until the tip emerges from within the vessel through the side wall. This rotation of the tool creates a second small hole in the side wall of the vessel. The distance between the first and second holes may be based on the length of the tip. For example, for a tool having a straight tip that is about 2.75 mm to about 3.00 mm in length, the resulting distance between the two small holes will be from about 2.75 mm to about 3.25 mm.

The vessel incision tool includes a sharp cutting blade to cut from hole to hole in the vessel. The tool may be rotated upward using a suture needle-like motion, thereby driving the cutting blade from the first small hole to the second small hole in the side wall. The tool is then removed from the vessel, and the incision is complete. The length of the incision may be altered to fit, for example, a connector that will be deployed at the site of the incision. For example, the perimeter of the incision created using the apparatus and methods described hereinabove may be identical to the perimeter of the expanded connector installed in the incision.

The controlled length incision created using the vessel incision tool of the present invention is effective for anastomoses such as, for example, anastomoses involving non-round connectors and for sutured anastomoses. Creating the incision allows a physician to inspect the incision and surrounding vessel for quality and disease prior to, for example, installing a connector at the site of the incision or sewing a graft to the vessel.

The tip and blade of the vessel incision tool may be constructed of any suitable rigid material, such as, for example, stainless steel. The blade of the vessel incision tool may be of any suitable shape, such as, for example, straight, curved, or any other shape suitable for cutting from the first hole to the second hole in the vessel side wall. The blade of the vessel incision tool may be at any suitable angle with respect to both the tip and the handle of the tool for different target sites.

Figure 1:
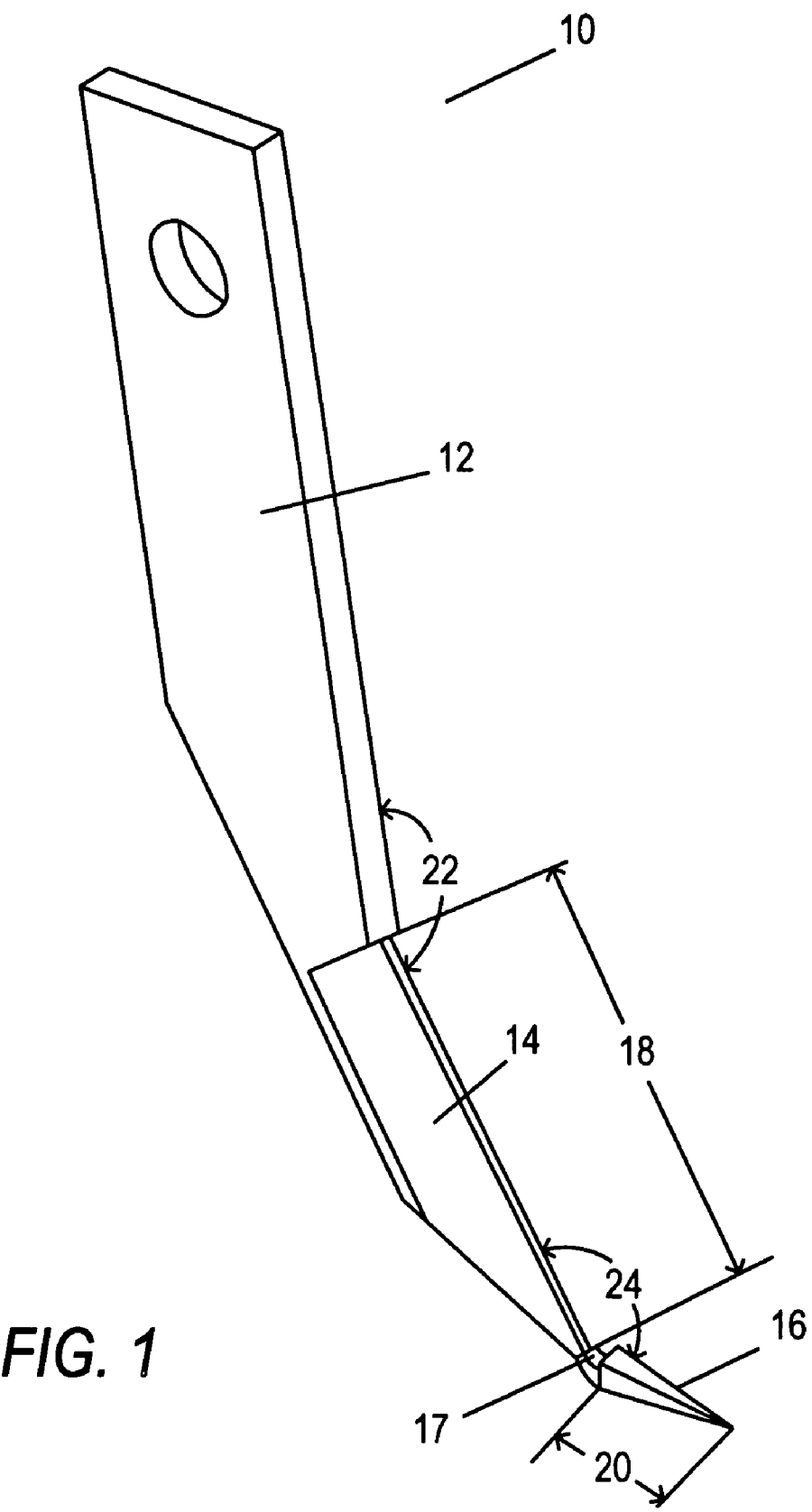
FIG. 1 is a perspective view of a vessel incision tool in accordance with the present invention.
Figure 5:
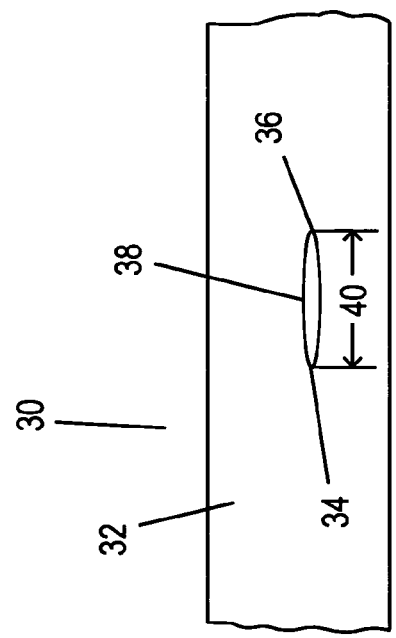
FIG. 5 is a perspective view illustrating a controlled-length incision created in a vessel using the procedure of FIGS. 2-4 in accordance with the present invention.

FIG. 1 is a perspective view of an illustrative vessel incision tool 10 in accordance with the present invention. Vessel incision tool 10 may include a handle 12, a blade 14, and a tip 16. Vessel incision tool 10 may include a recess 17 between tip 16 and blade 14 that indicates to a physician when tip 16 has been inserted far enough into a vessel. Blade 14 and tip 16 have respective lengths 18 and 20. In one illustrative example, length 18 may be approximately 6.4 mm, and length 20 may be approximately 2.5 mm. Handle 12 and blade 14 form an angle 22, and blade 14 and tip 16 form an angle 24. As described hereinabove, angles 22 and 24 may be adjusted to accommodate different target sites.

Figure 4:
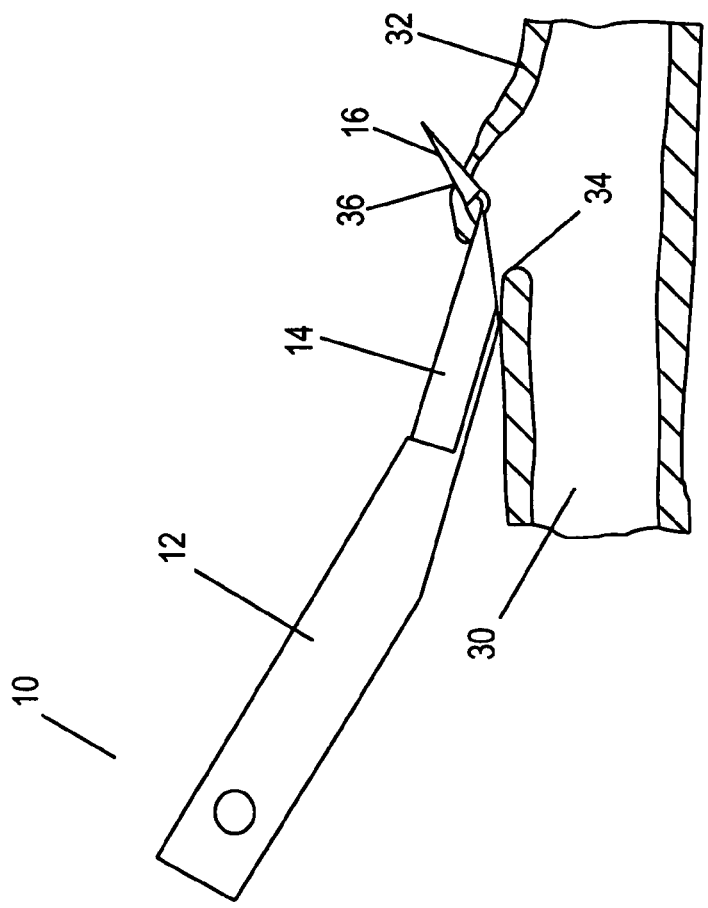
FIG. 4 is a view similar to FIG. 3 illustrating a later stage of a procedure in accordance with the present invention.

FIGS. 2-5 illustrate a method for creating a controlled length incision in a vessel using, for example, vessel incision tool 10 of FIG. 1. As shown in FIG. 2, sharp tip 16 of tool 10 may be inserted through side wall 32 of vessel 30. Tip 16 may be inserted through side wall 32 as far as recess 17. The insertion of tip 16 through side wall 32 results in the creation of a first hole 34. To achieve the orientation of FIG. 3, tool 10 may be rotated such that sharp tip 16 is forced through side wall 32, thereby creating a second hole 36. The distance from second hole 36 to first hole 34 is approximately equal to length 20 (FIG. 1) of tip 16. After tip 16 has emerged from within vessel 30, tool 10 may be rotated upward such that cutting blade 14 cuts from first hole 34 to second hole 36, as shown in FIG. 4. This results in the creation of an incision 38 having a controlled, predetermined length 40, as shown in a top down view in FIG. 5. As stated hereinabove, length 40 of incision 38 may be approximately equal to length 20 (FIG. 1) of tip 16.

Figure 7:
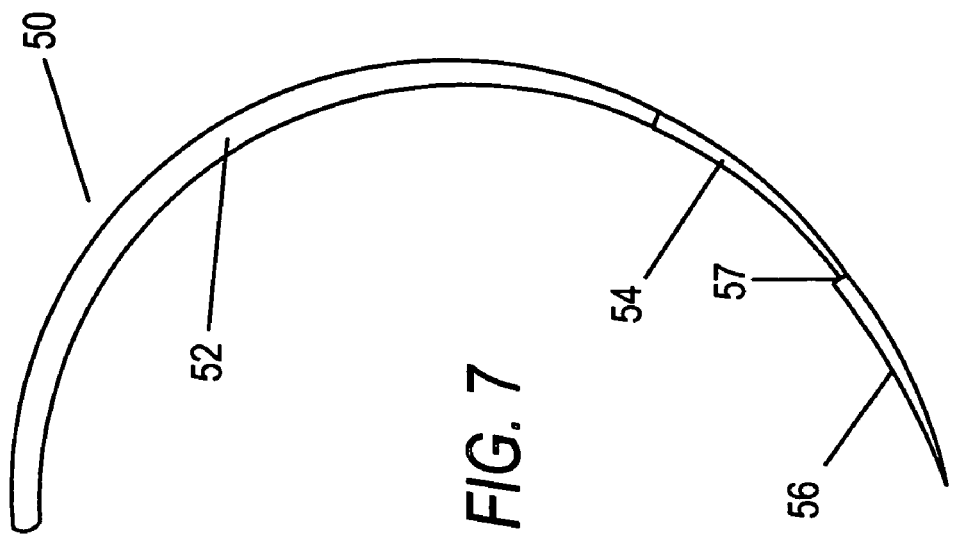
FIG. 7 is another perspective view of the vessel incision tool of FIG. 6 in accordance with the present invention.
Figure 6:
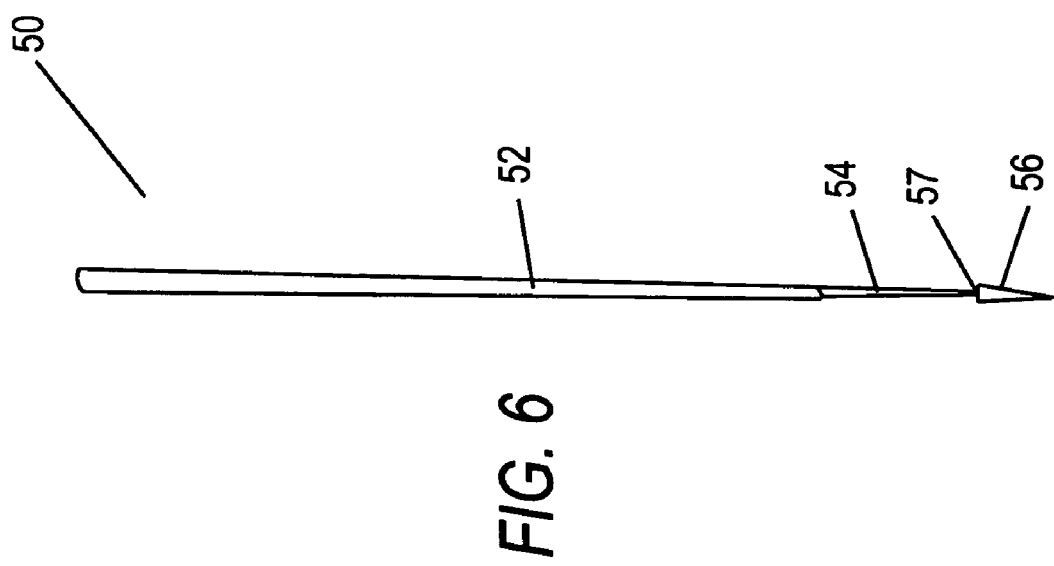
FIG. 6 is a perspective view of another vessel incision tool in accordance with the present invention.

FIGS. 6 and 7 are perspective views of another illustrative vessel incision tool 50 in accordance with the present invention. FIG. 6 shows tool 50 as rotated 90-degrees into the page from the orientation of FIG. 7. Vessel incision tool 50 has a certain curvature which may be constant or may vary along the length of the tool. The curvature of tool 50 may be such that tool 50 is suitable for a particular target site. Vessel incision tool 50 may include a handle 52, a blade 54, and a tip 56. Tool 50 may include a recess 57 between tip 56 and blade 54 that indicates to a physician when tip 56 has been inserted far enough into a vessel. Blade 54 and tip 56 of vessel incision tool 50 may be constructed of any suitable material such as, for example, stainless steel.

Vessel incision tool 50 may be used to create a controlled length incision in a vessel in a manner substantially similar to that described hereinabove in connection with FIGS. 2-5.

In some embodiments of the present invention, a connector may be installed in an incision in a target vessel. An assembly that includes another connector and a graft conduit may be coupled to the connector in the target vessel. For simplicity, the connector installed in the incision in the target vessel will be referred to hereinafter as the "target vessel connector," and the connector assembled with the graft conduit will be referred to hereinafter as the "graft connector." One or both of the target vessel and the graft vessel may be small diameter vessels. The incision into which the target vessel connector is inserted may be created using the apparatus and methods described hereinabove for creating an incision having a controlled, predetermined length.

By inserting a target vessel connector into the incision in the target vessel, a physician may first create and inspect connector assemblies for each vessel (e.g., an assembly that includes the target vessel connector and target vessel, and an assembly that includes the graft connector and graft conduit), and then couple the two assemblies to one another. Although the target vessel connector will continue to be referred to herein as a "connector," in actuality the target vessel connector may be any structure that serves to hold the incision in the target vessel open and to keep the tissue layers of the vessel together. The target vessel connector may be similar to, for example, an internal traction device that remains permanently in place. The target vessel connector is mounted in the target vessel without another vessel (e.g., a graft conduit) attached to it.

Apparatus and methods of the present invention for installing a target vessel connector having a cellular structure in a target vessel include inserting the first connector into an incision in the target vessel using a delivery device. (It should be noted that the incision in the target vessel, and any other incision referred to herein, may also be referred to as an "aperture.") After inserting the target vessel connector into the incision, the cellular structure of the connector may be expanded in the axial direction of the target vessel, resulting in perimeter-matching (e.g., the perimeter of the target vessel connector approaches the perimeter of the incision) and hook-shortening (e.g., "fangs" of the first connector that are situated inside and outside of the target vessel advance toward one another as the cellular structure is axially expanded). The cellular structure of the first connector may be expanded in the radial direction of the target vessel, resulting in the desired connector shape and cross-section for the lumen of the graft vessel. The delivery device may then be removed after the target vessel connector has been expanded in both the axial and radial directions. The resulting anastomosis may be inspected by the physician for attributes such as, for example, placement, disease, and lumen integrity.

Target vessel connector structures for use with apparatus and methods of the present invention may be expanded radially and axially to create, for example, a non-round structure, stable expansion in one plane, and a shortening of the gap between the internal fingers (i.e., the fingers that engage the inner surface of the target vessel) and external fingers (i.e., the fingers that engage the outer surface of the target vessel). In an illustrative example, a starting gap between internal and external fingers of the target vessel connector may be approximately 0.060 inches, and a finished gap may be approximately 0.010 inches. In the same illustrative example, a starting perimeter of the target vessel connector may be approximately 0.250 inches, and a finished perimeter may be approximately 0.650 inches.

In one example, this expanded connector structure may create a known perimeter to which a graft connector may be connected. The expanded connector structure may hold the layers of the target vessel together to allow further manipulation of the target vessel without delamination or dissection of the tissue. The expanded connector structure may allow for the management of any disease present in the target vessel.

The installation of a target vessel connector in the incision in the target vessel allows for different coupling options between the target vessel connector and graft connector. For example, the graft connector and graft conduit assembly may encapsulate the target vessel connector.

The target vessel connector may be round or non-round. In some embodiments of the present invention, the target vessel connector may include external hooks to couple the target vessel connector to the graft connector.

FIG. 8 shows an illustrative target vessel connector 100 that may be installed in a controlled-length incision in a target vessel in accordance with the present invention. Illustrative connectors similar to those that may be used in accordance with the present invention are described in, for example, Swanson et al. U.S. Pat. No. 6,602,263, and U.S. patent publication No. US 2002/0183769, published Dec. 5, 2002, which are both hereby incorporated by reference herein in their entireties.

FIG. 8 shows a planar development of what is actually, preferably, an integral, one-piece (unitary), annular connector 100. In particular, the left and right edges of the structure shown in FIG. 8 are actually, preferably, joined to and integral with one another. Thus, the actual structure is as shown in FIG. 9, although FIG. 8 is useful to more clearly reveal certain details of various features of connector 10.

A particularly preferred material for connector 100 is stainless steel (e.g., 316 stainless steel). Other examples of suitable materials include tantalum, tungsten, platinum, other steels, and nickel titanium alloy ("nitinol"). Connector 100 may be advantageously produced by starting with a single, unitary metal tube, such as a hypotube, and removing selected material until only the structure show in FIG. 9 remains. For example, laser cutting may be used to remove material from the starting tube in order to produce connector 100.

Connector 100 may include annularly spaced cell portions 102. Accordingly to one embodiment, connector 100 includes six repeating cell portions 102. Connector 100 may have fewer or more than six of cell portions 102, depending on the diameter of tube used to manufacture connector 100 and the resulting enlarged perimeter desired.

Some or all of cell portions 102 may include an internal member 104 that in this example has a free end portion 106 that is sharply pointed. In one example, internal member 104 may have a length 108 of about 0.35 mm. However, the dimensions of internal member 104 may be altered according to the wall thickness of the target vessel wall. Each of internal members 104 is deflectable radially outward from the remainder of the structure of connector 100, as shown, for example, in FIG. 9.

Some or all of cell portions 102 may also include an external member 110 that in this case has a barbed free end portion 112 that is sharply pointed. In one example, external member 110 may have a length 113 of about 0.55 mm. However, the dimensions of external member 110 may be altered according to the thickness of the target vessel wall. Each of external members 110 is deflectable radially outward from the remainder of the structure of connector 100, as shown, for example, in FIG. 9.

The above-mentioned outward deflection of internal members 104 and external members 110 may be produced by putting connector 100 on a mandrel and prying members 104 and 110 radially outward. Following deflection of members 104 and 110, an initial axial spacing 114 may be defined therebetween. Spacing 114 may vary depending on the wall thickness of the target vessel into which connector 100 is to be installed.

Figure 10:
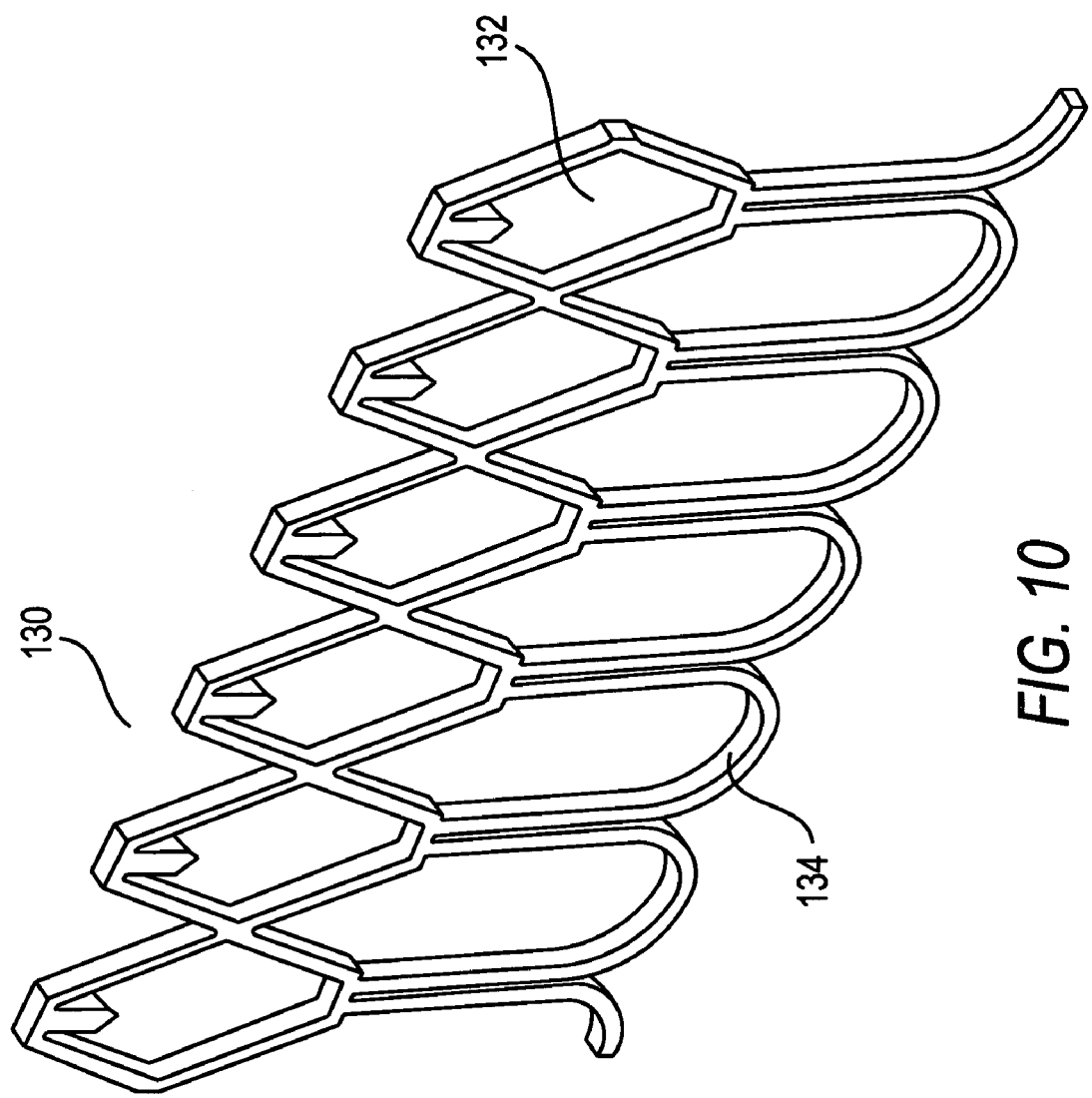
FIG. 10 is a planar development of another target vessel connector structure in accordance with the present invention.
Figure 11:
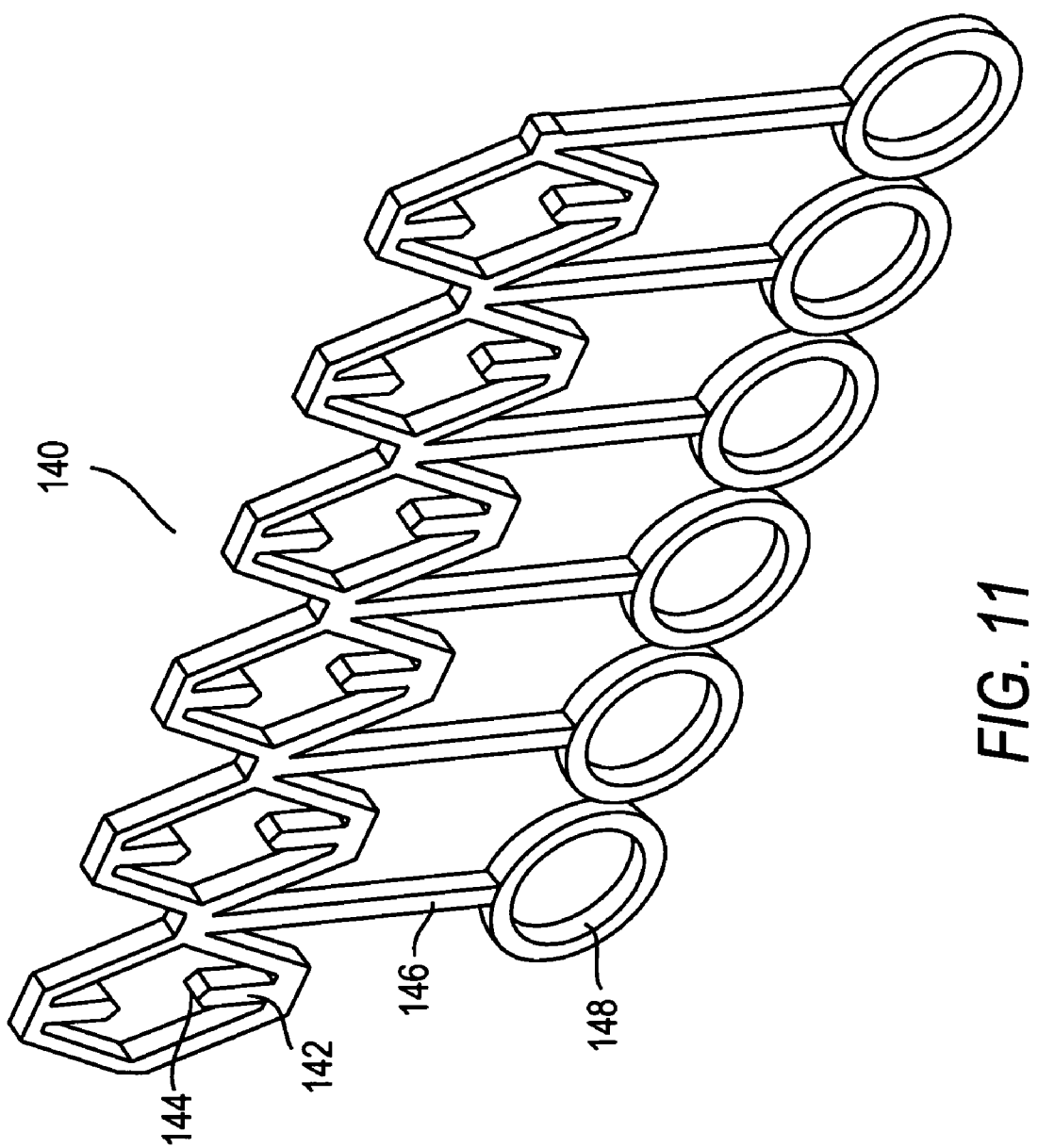
FIG. 11 is a planar development of yet another target vessel connector structure in accordance with the present invention.
Figure 12:
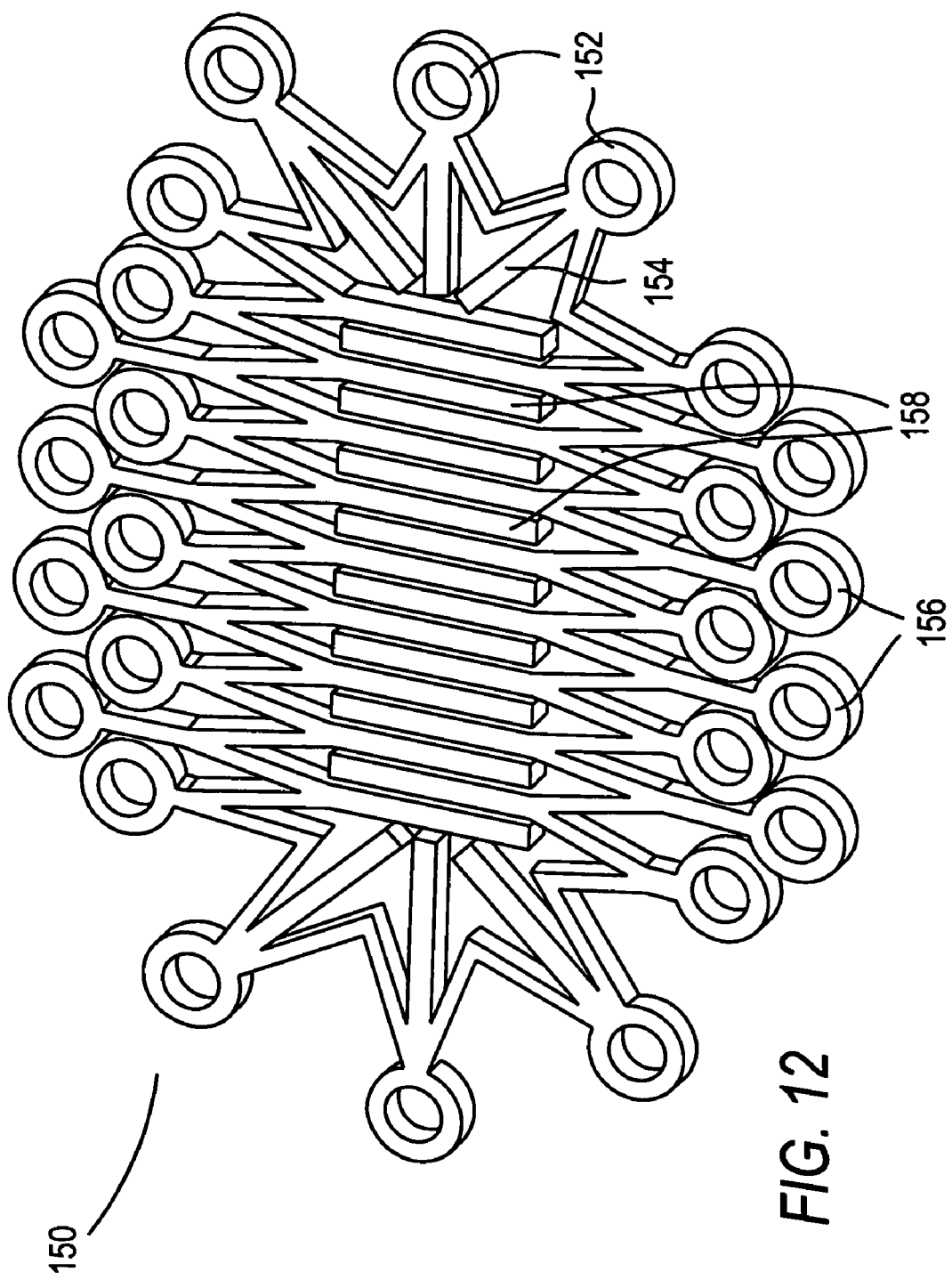
FIG. 12 is a planar development of still another target vessel connector structure in accordance with the present invention.

Various alternative embodiments of a connector in accordance with the present invention are now described in connection with FIGS. 10-12. The connectors in FIGS. 10-12 (shown in planar development) are all suitable for installation in an incision in a target vessel. The connectors of FIGS. 10-12 are of a similar size as connector 100 (FIGS. 8 and 9), and the connectors are constructed of the same material or materials as connector 100. The differences between the embodiments of connectors shown in FIGS. 10-12 and connector 100 are made apparent in the description that follows.

An illustrative embodiment of a connector 130 in accordance with the present invention is shown in FIG. 10. Rather than having barbed external members such as external members 110 of connector 100 (FIG. 8), connector 130 has U-shaped external members 134. One end of an external member 134 may be attached to one cell portion 132, and the other end of member 134 may be attached to an annularly adjacent cell portion 132. U-shaped members 134 may engage the outside wall of the target vessel after connector 130 has been installed in the incision in the vessel. U-shaped members 134 may improve the rigidity of connector 130. For example, members 134 may prevent a cell portion 132 from twisting with respect to the two annularly adjacent cell portions 132.

An illustrative embodiment of a connector 140 in accordance with the present invention is shown in FIG. 11. Rather than having barbed external members such as external members 110 of connector 100 (FIG. 8), connector 140 has external members 142 with sharpened free ends 144. In addition, connector 140 has additional external members 146 having looped end portions 148. External members 146 may engage the outside wall of the target vessel after connector 140 has been installed in the incision in the vessel.

An illustrative embodiment of a connector 150 in accordance with the present invention is shown in FIG. 12. Connector 150 has differing external and internal members for the portions of the connector that will be oriented toward differing portions of the incision in the target vessel. Referring back to FIG. 5, incision 40 spans from point 34 to point 36. Connector 150 may be installed in such an incision, and may be expanded in both the radial and axial directions of the target vessel such that a non-round anastomotic connection results. (The installation of a target vessel connector in a target vessel will be discussed in detail hereinbelow.) For example, the resulting anastomotic connection may be elliptical in shape. Thus, referring back to FIG. 12, external members 152 and internal members 154 may be positioned at the "ends" of the elliptical opening, and external members 156 and internal members 158 may be positioned along the "sides" of the elliptical opening. In function, external members 152 and 156, and internal members 154 and 158, all engage the side wall of the target vessel.

In some embodiments of the present invention, a delivery device for installing a connector in an incision in a vessel may be provided. In one example, the delivery device may include anvil heads that plastically deform a connector axially, by the anvil heads moving along the axis of the target vessel (i.e., in the axial direction), and radially, by the anvil heads moving outward in the radial direction of the target vessel. The delivery tool may include built-in "stops" that control the amount of axial and radial expansion caused by the delivery device.

In another example, the delivery device may shield internal members of the target vessel connector for introduction into the target site incision. In still another example, the delivery device may allow a physician to visually and tactilely deploy the device into all combinations of target sites on a patient's heart. In another example, friction between the connector and the delivery device may be minimized (e.g., by altering the design of the anvils), thereby allowing for uniform expansion of the connector. In another example, the delivery device may result in maximum cell expansion with minimal user effort by, for example, applying the principles of "mechanical advantage."

Delivery actuation may be at the connector or at some location remote to the connector, such as a location outside of the patient's chest cavity. The actuation may be caused by direct force or may be, for example, cable driven, hydraulic, or caused by any other suitable force.

FIGS. 13 and 14 show an illustrative delivery device 170 in accordance with the present invention.

FIG. 13 is a perspective view showing the entirety of delivery device 170, and FIG. 14 is an enlarged perspective view showing a portion of the delivery device in more detail. Delivery device 170 may include a rotating handle portion 172 and a sheath portion 174 that encapsulates the distal end of the handle portion. Delivery device 170 includes an anvil structure 180 and an anvil structure 182. Anvil structure 180 may include an elongated member 181 that is fixed within sheath portion 174. Anvil structure 182 may include an elongated member 183 that is attached to handle portion 172. Anvil structure 182 may move with respect to anvil structure 180 as controlled by handle portion 172. Handle portion 172 may rotate in directions 176 and 178, thereby moving anvil structure 182 away from and toward anvil structure 180 in the radial direction of sheath portion 174. Handle portion 172 may move in directions 184 and 186, thereby moving anvil structure 182 away from and toward anvil structure 180 in the axial direction of sheath portion 174.

In some embodiments of the present invention, a connector structure may be disposed annularly around elongated members 181 and 183 for installation into an incision in a patient's body tissue conduit. To expand the connector, handle portion 172 may be rotated in one or both of directions 176 and 184, which moves anvil structure 182 away from anvil structure 180 in both the radial and axial directions of sheath portion 174. For insertion into an incision in a body tissue conduit, one or both of anvil structures 180 and 182 may shield tissue engagement members of the connector to prevent the members from snagging on the incision.

Figure 19:
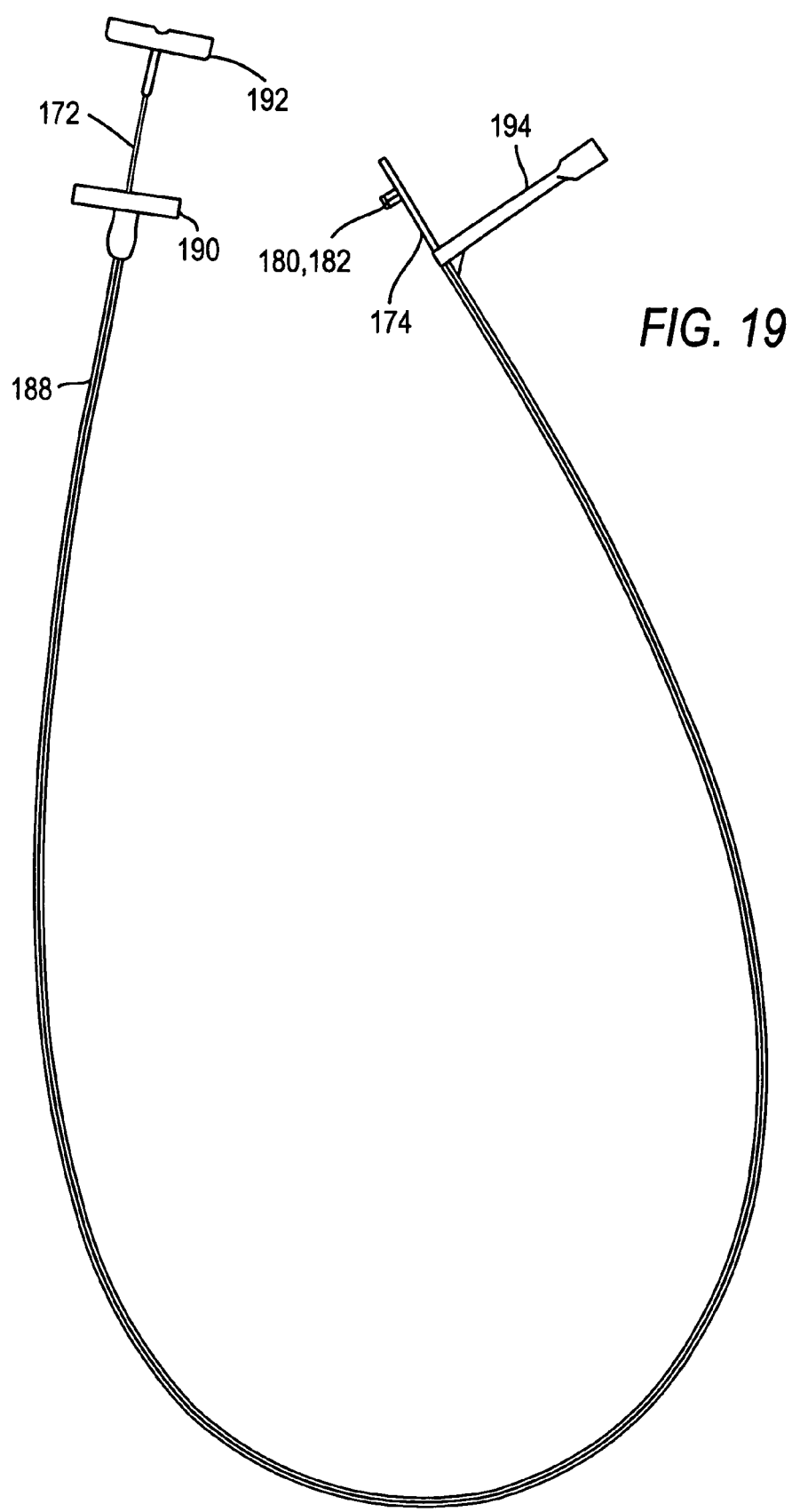
FIG. 19 is a perspective of an alternative embodiment of the delivery device of FIGS. 13 and 14 in accordance with the present invention.

Referring to FIG. 19, an embodiment of delivery device 170 is shown in which the device may be actuated remotely. As shown in FIG. 19, handle portion 172 may be disposed annularly within an outer catheter 188. Outer catheter 188 and handle portion 172 may have grips 190 and 192, respectively. Outer catheter 188 may be guided through a patient's vasculature to the target site at which the connector is to be installed. Once anvil structures 180 and 182 are near the target site, a device (e.g., forceps) may be used to aid in positioning the anvil structures, and therefore the connector, within the target site incision. It should be noted that bar 194 will not be present in embodiments of delivery device 170 that allow for remote actuation. However, bar 194 may be present in non-remote actuation embodiments to aid in positioning anvil structures 180 and 182 within the target site incision.

Figure 16:
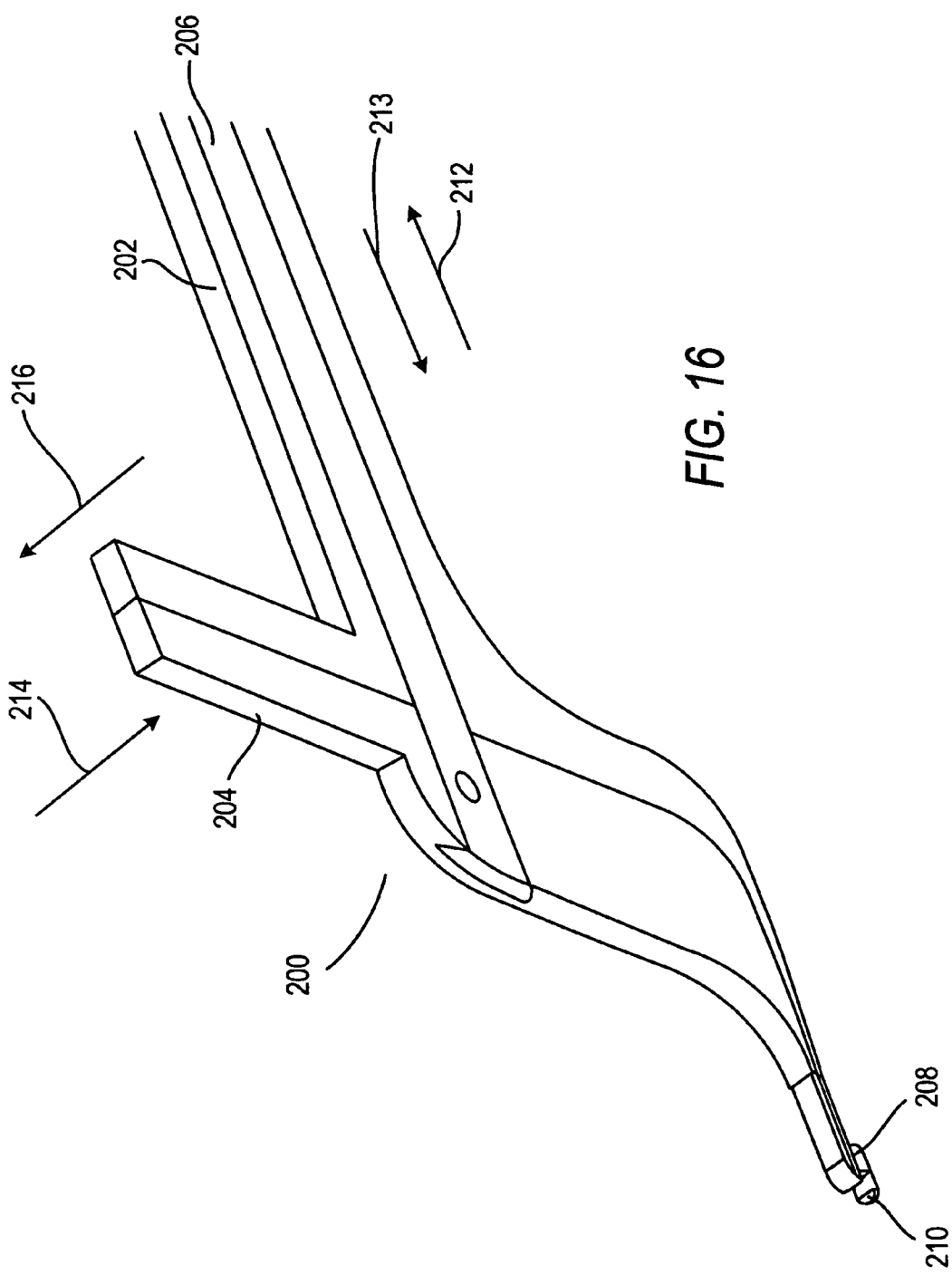
FIG. 16 is another perspective view of the delivery device of FIG. 15 in accordance with the present invention.

FIGS. 15 and 16 show another illustrative delivery device 200 in accordance with the present invention. Delivery device 200 may includes movable handle portion 202 and a fixed portion 204. Delivery device 200 may include anvil structures 208 and 210. Anvil structure 208 may include an elongated member 209 attached to handle portion 202, and anvil structure 210 may include an elongated member 211 attached to fixed portion 204. Handle portion 202 may be movable about a member 206 that is attached to fixed portion 204. Handle portion 202 may move in directions 213 and 212, thereby moving anvil 208 toward and away from anvil 210 in directions 213 and 212. Handle portion 202 may move in directions 214 and 216, thereby moving anvil 208 away from and toward anvil 210 in directions 216 and 214.

As described hereinabove in connection with delivery device 170, in some embodiments of the present invention, a connector structure may be disposed annularly around elongated members 209 and 211 of anvil structures 208 and 210, respectively, for installation into an incision in a patient's body tissue conduit. To expand the connector, handle 202 may be moved in one or both of directions 212 and 214, which moves anvil 208 away from anvil 210 in directions 212 and 216. For insertion into an incision in a body tissue conduit, one or both of anvils 208 and 210 may shield tissue engagement members of the connector to prevent the members from snagging on the incision.

Figure 17:
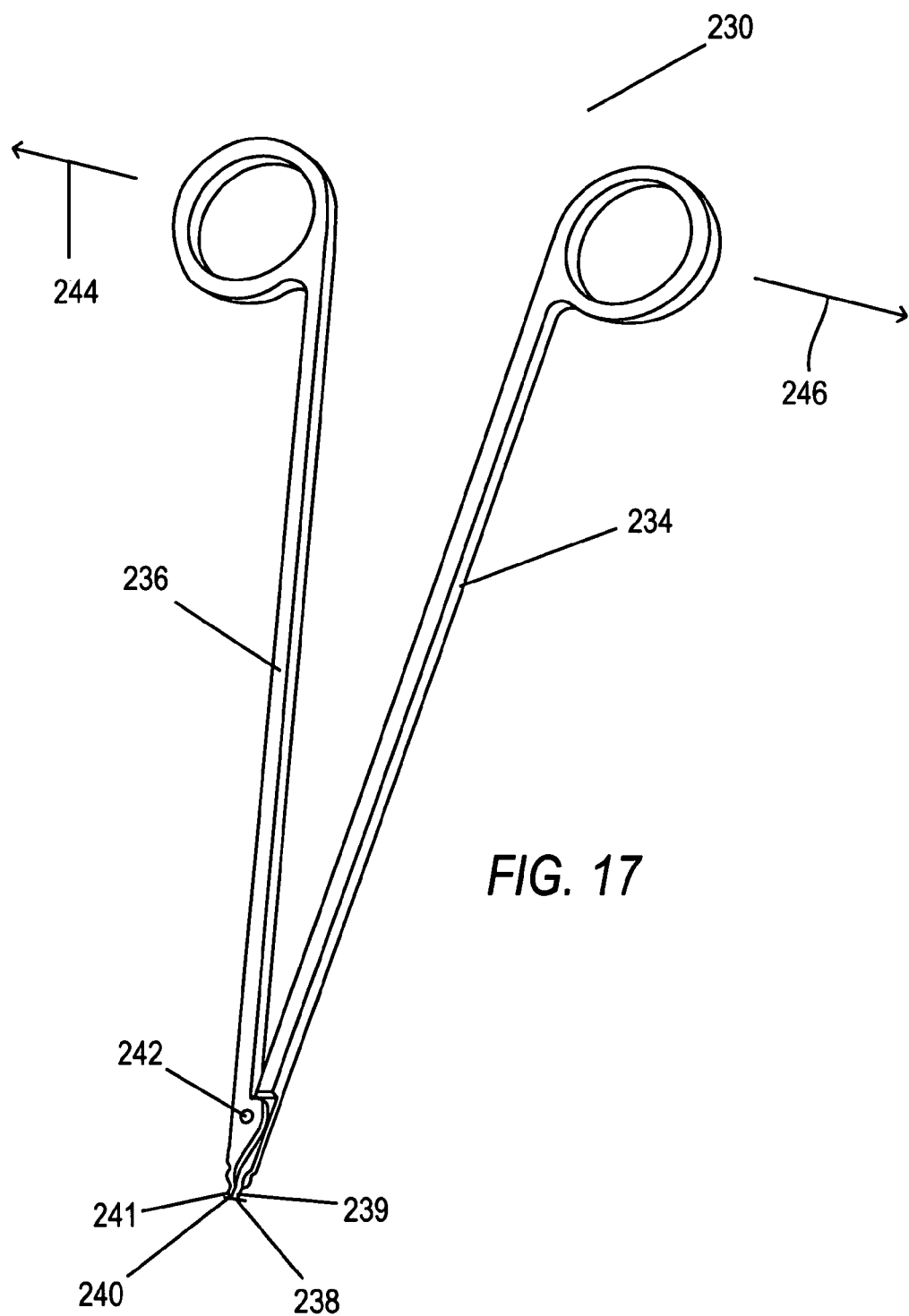
FIG. 17 is a perspective view of yet another delivery device in accordance with the present invention.

FIG. 17 shows yet another illustrative delivery device 230 in accordance with the present invention. Delivery device 230 may include movable handle members 234 and 236. Delivery device 200 may include anvil structures 238 and 240. Anvil structure 238 has an elongated member 239 that is attached to handle member 234. Anvil structure 240 has an elongated member 241 that is attached to handle member 236. Handle members 234 and 236 are movable about a pivot point 242. Handle members 234 and 236 may move away from one another in directions 246 and 244, respectively, thereby moving anvils 238 and 240 away from one another in the same directions. (It should be noted that one of handle members 234 and 236 may remain fixed, while the other handle member moves with respect to the fixed member. It is for illustration only that this example is described as if both members 234 and 236 move about pivot point 242.) In some embodiments of the present invention, handle members 234 and 236 may rotate about pivot point 242 such that, in the orientation illustrated in FIG. 17, one member moves out of the page and the other member moves into the page.

As described hereinabove in connection with delivery devices 170 and 200, in some embodiments of the present invention, a connector structure may be disposed annularly around elongated members 239 and 241 of anvil structures 238 and 240, respectively, for installation into an incision in a patient's body tissue conduit. To expand the connector, handle members 234 and 236 may be moved in directions 246 and 244, which moves anvils 238 and 240 away from one another in directions 246 and 244. As stated hereinabove, handle members 234 and 236 may also rotate about attachment point 242 both into and out of the page of FIG. 17, thereby expanding the connector. Alternatively, delivery device 230 may be rotated 90°, and handle members 234 and 236 may again move away from one another in directions 246 and 244, respectively. For insertion into an incision in a body tissue conduit, one or both of anvil structures 238 and 240 may shield tissue engagement members of the connector to prevent the members from snagging on the incision.

Figure 18:
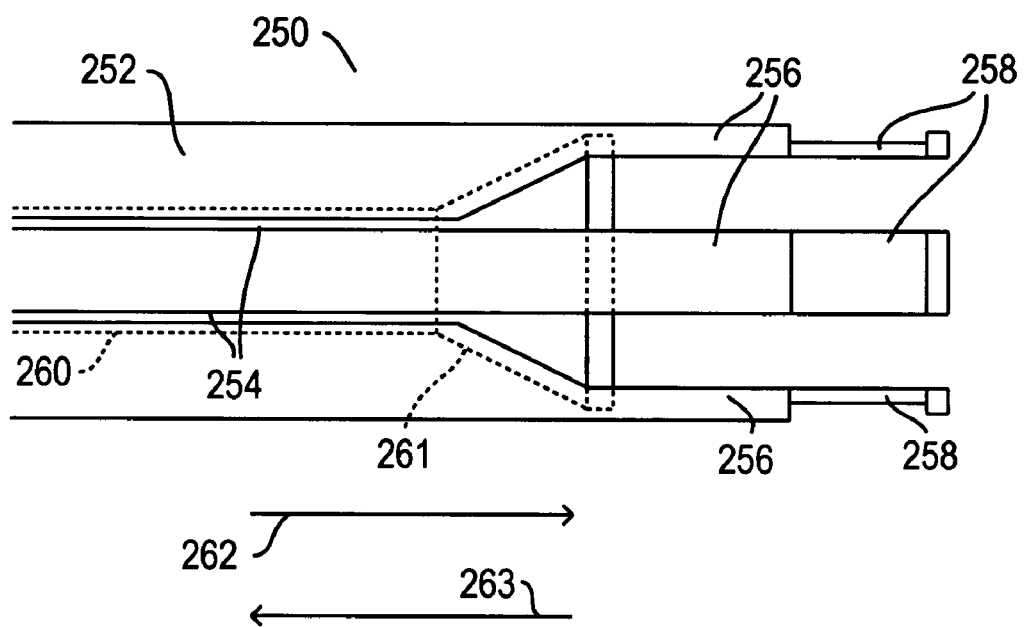
FIG. 18 is a perspective view of still another delivery device in accordance with the present invention.

FIG. 18 shows still another delivery device 250 in accordance with the present invention. Delivery device 250 may include outer member 252 having multiple slits 254. In the example of FIG. 18, outer member 252 has four slits 254, creating four "fingers" 256. Each finger 256 may have a notch 258. Outer member 252 includes a tapered hole within which an inner member 260 that has a cone 261 at its distal end resides.

Inner member 260 may move in directions 262 and 263, toward and away from notches 258, respectively. When inner member 260, and therefore cone 261, is pulled in direction 263 away from notches 258, fingers 256 are urged radially out from their original positioning. In some embodiments of the present invention, a connector structure may be disposed annularly around outer member 252 in notches 258. Thus, when cone 261 moves away from notches 258 in direction 263, the connector structure may expand due to the outward movement of fingers 256. Cone 261 may have any suitable shape to effect the desired expansion of the connector structure. For example, if a non-round expansion of the connector structure is desired, cone 261 may have a non-round shape (e.g., an oval shape).

FIGS. 20-24 illustrate a method for installing a target vessel connector in an incision in a target vessel using, for example, delivery device 170 of FIGS. 13 and 14 in accordance with the present invention. The target vessel may be a vessel having a small diameter.

An incision 304 may be made in a side wall 302 of target vessel 300 in a manner such as that described hereinabove in connection with FIGS. 2-5. Alternatively, incision 304 may be made in vessel 300 using any other suitable technique, such as that described in published Patent Cooperation Treaty ("PCT") patent publication No. WO 01/39672, published Jun. 7, 2001, which is hereby incorporated by reference herein in its entirety. (It should be noted that incision 304 into which a target vessel connector may be installed, and any other incision into which a connector structure may be installed, may also be referred to herein as an "aperture.")

Figure 20:
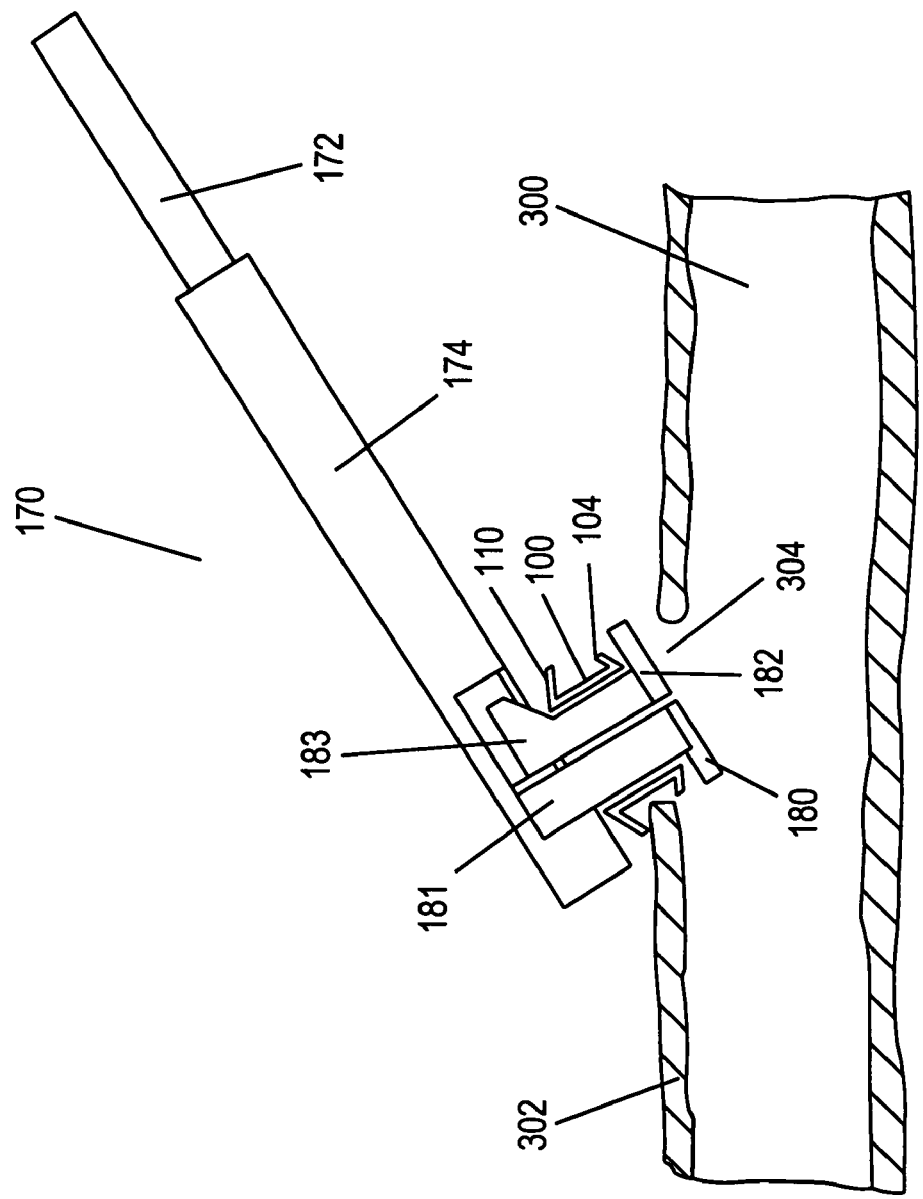
FIG. 20 is a sectional view illustrating a stage of a procedure involving the delivery device of FIGS. 13 and 14 and the target vessel connector structure of FIGS. 8 and 9 in accordance with the present invention.
Figure 21:
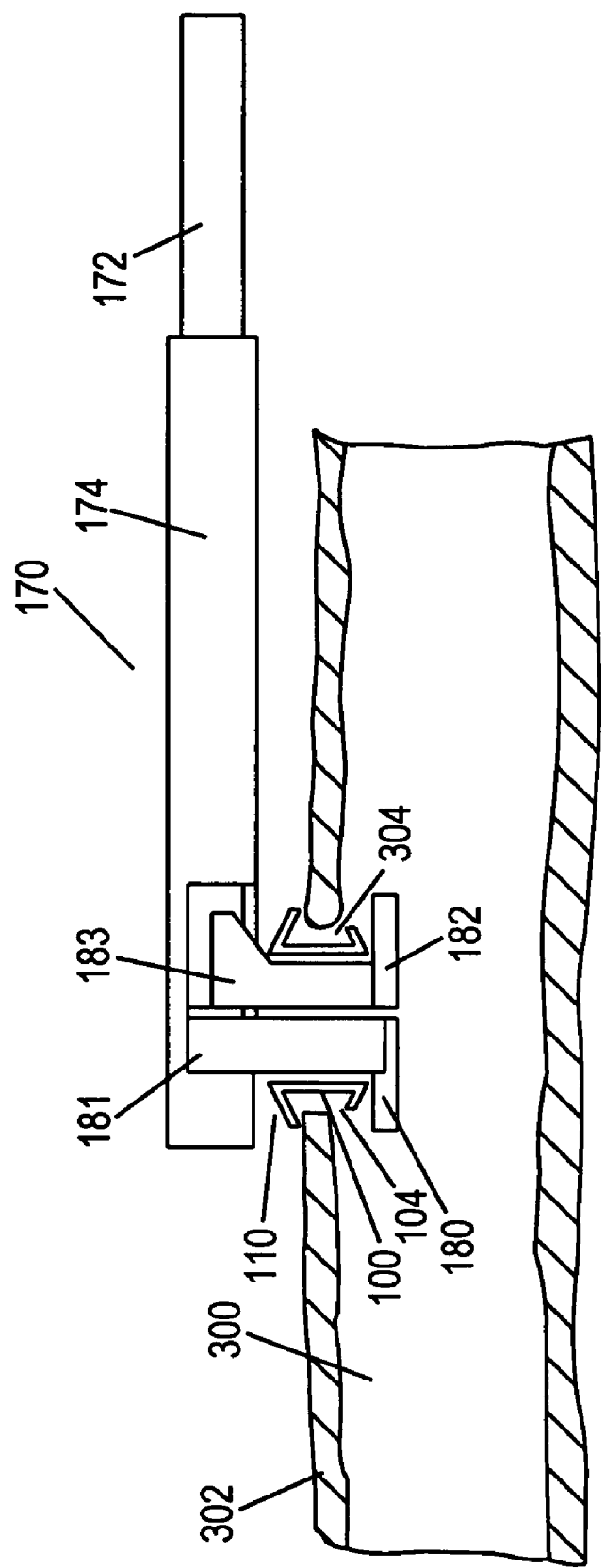
FIG. 21 is a view similar to FIG. 20 illustrating a further stage of a procedure in accordance with the present invention.
Figure 22:
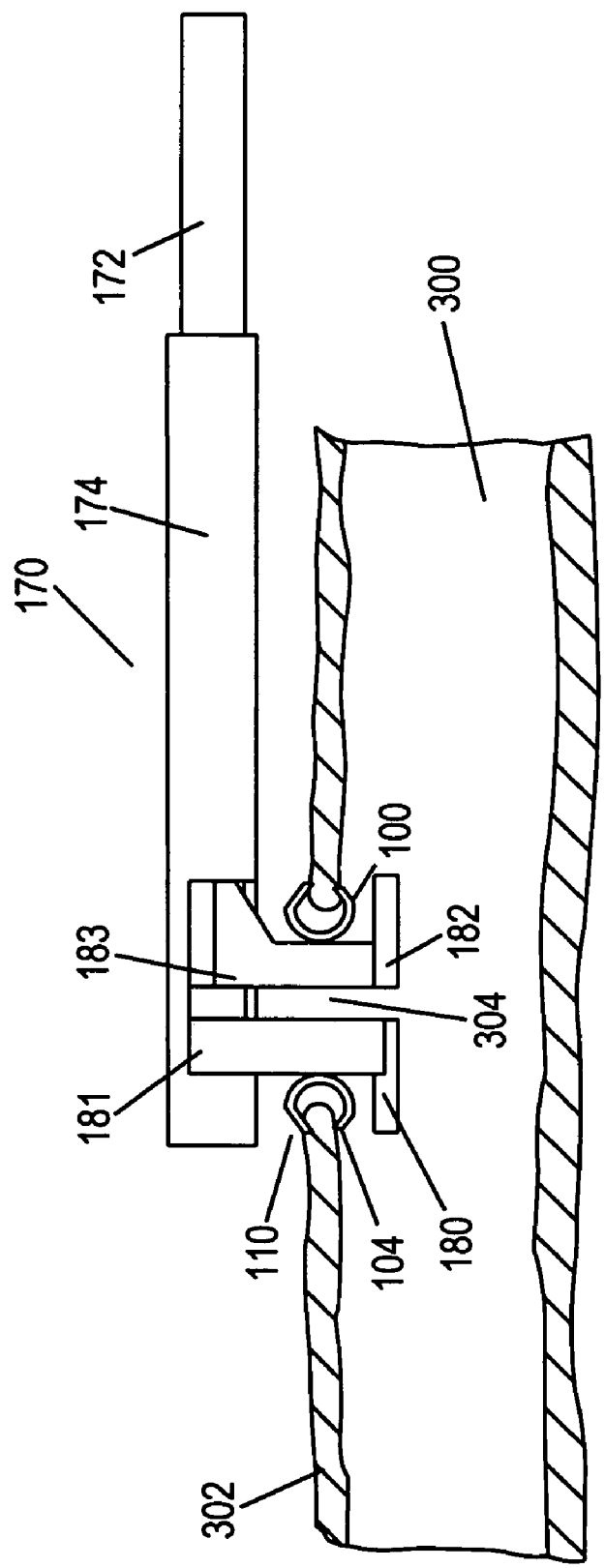
FIG. 22 is a view similar to FIG. 21 illustrating a later stage of a procedure in accordance with the present invention.
Figure 23:
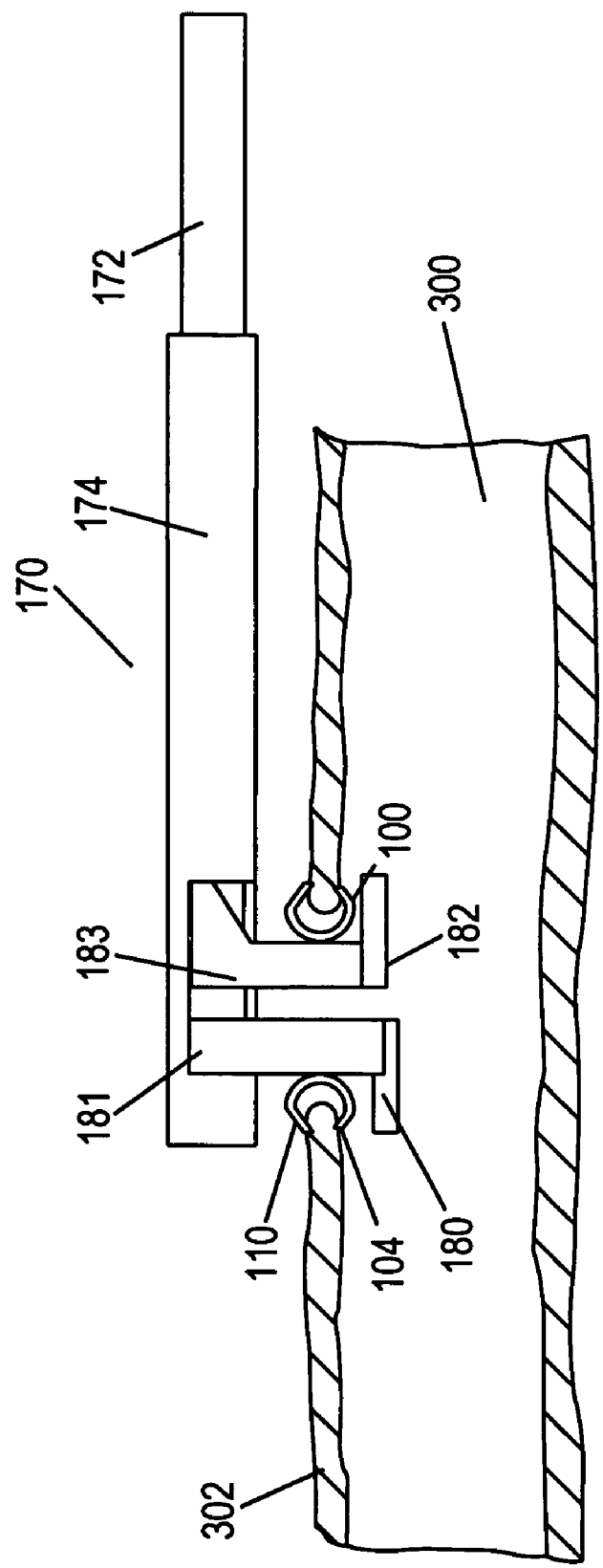
FIG. 23 is a view similar to FIG. 22 illustrating a still later stage of a procedure in accordance with the present invention.

As shown in FIG. 20, a connector such as connector 100 (FIGS. 8 and 9) may be disposed annularly around elongated members 181 and 183 of delivery device 170. Anvil structure 180 may be inserted into incision 304 at some angle to prevent snagging side wall 302 on internal members 104. Anvil structure 182 may then be inserted into incision 304, attaining the configuration shown in FIG. 21. It should be noted that, while the example illustrated in FIGS. 20 and 21 shows anvil 180 entering incision 304 prior to anvil 182, this is merely for illustration. Either anvil structure 180 or anvil structure 182 may enter incision 304 prior to the other anvil structure.

Figure 24:
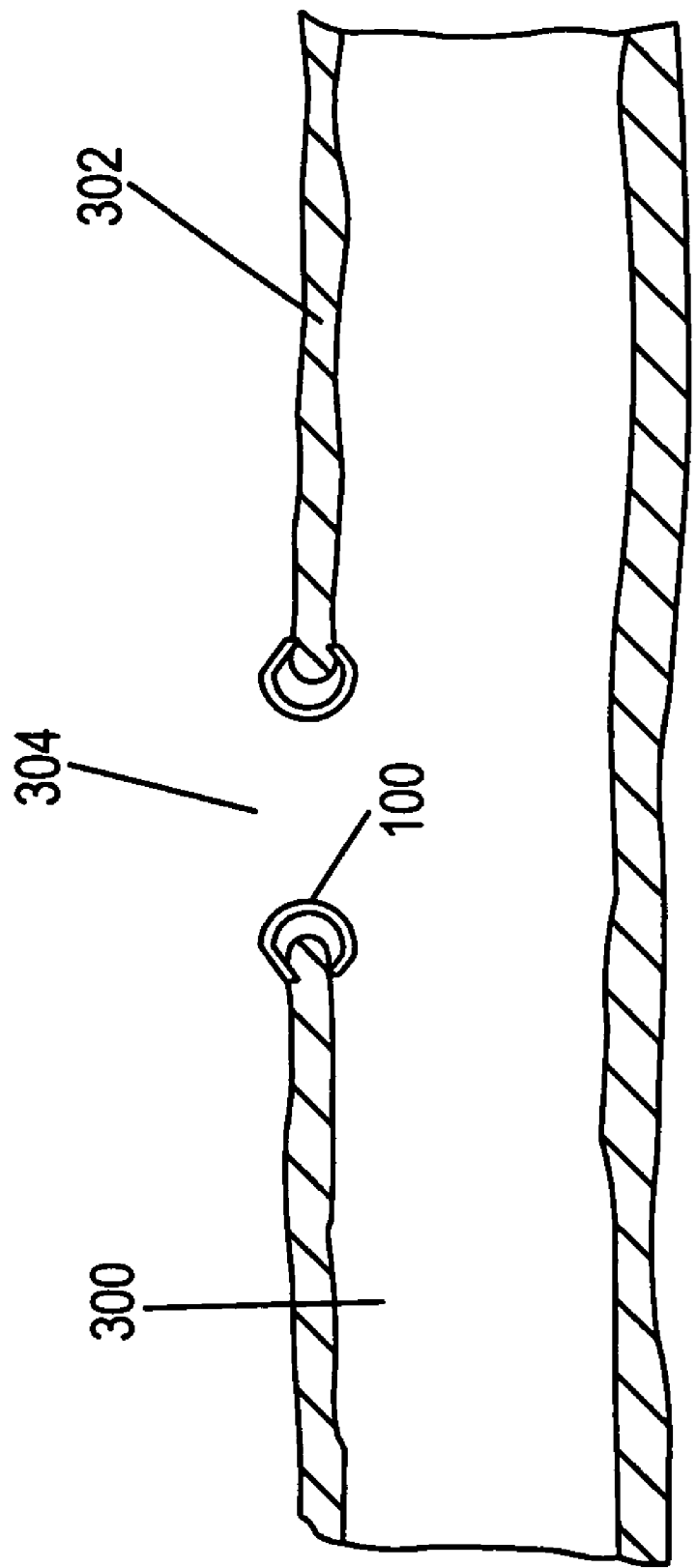
FIG. 24 is a view similar to FIG. 23 illustrating a later stage of a procedure in accordance with the present invention.

After connector 100 has been encapsulated within incision 304, as shown in FIG. 21, the connector may be expanded such that members 104 and 110 engage side wall 302. To expand connector 100 in the axial direction of target vessel 300, handle portion 172 of delivery device 170 may be pulled in direction 184 (FIG. 13), resulting in the configuration shown in FIG. 22. To expand connector 100 in the radial direction of target vessel 300, handle portion 172 of delivery device 170 may be rotated in direction 176 (FIG. 13), resulting in the configuration shown in FIG. 23. Delivery device 170 may then be removed, resulting in the configuration shown in FIG. 24. (It will be appreciated that FIG. 24 is greatly simplified in that it only shows the portion of connector 100 that is in the plane of the page on which FIG. 24 is drawn. Connector 100 is in fact fully annular all the way around incision 304 in side wall 302 of target vessel 300.) In some embodiments of the present invention, connector 100 may be expanded in the axial direction of target vessel 300 more than it is expanded in the radial direction of the target vessel. This difference in expansion results in a non-round (e.g., oval) expanded connector 100.

By expanding connector 100 in both the axial and radial directions of target vessel 300, both inner members 104 and outer members 110 engage side wall 302 of vessel 300. Preferably, both inner members 104 and outer members 110 penetrate the inner and outer surfaces, respectively, of side wall 302 around the periphery of incision 304. Alternatively, one or both of inner members 104 and outer members 110 may engage, but not penetrate, the inner and outer surfaces, respectively, of side wall 302.

Anvil structures 180 and 182, and any of the other anvil structures described herein in connection with other embodiments of the delivery device of the present invention, may be of any suitable shape in order to achieve the desired expanded configuration of connector 100.

It should be noted that, while the example of FIGS. 20-24 is shown using delivery device 170, this is merely illustrative, and any suitable delivery device may be used to install a target vessel connector in an incision in a target vessel. For example, any of the delivery devices shown in FIGS. 15-19 may be used to install a connector in an incision in a target vessel.

As described hereinabove, a connector structure (e.g., connector 100 of FIGS. 8 and 9) may be installed in an incision in a target vessel. The installation of a structure such as a connector in the target vessel incision may, for example, create a known perimeter to which a graft assembly may be attached, hold the tissue layers of the target vessel together to allow further manipulation of the target vessel without delamination or dissection, or allow a physician to manage any existing disease. As an alternative to installing a connector structure in the target vessel incision, other structures may be installed in the incision that perform some or all of the functions provided hereinabove.

Figure 25:
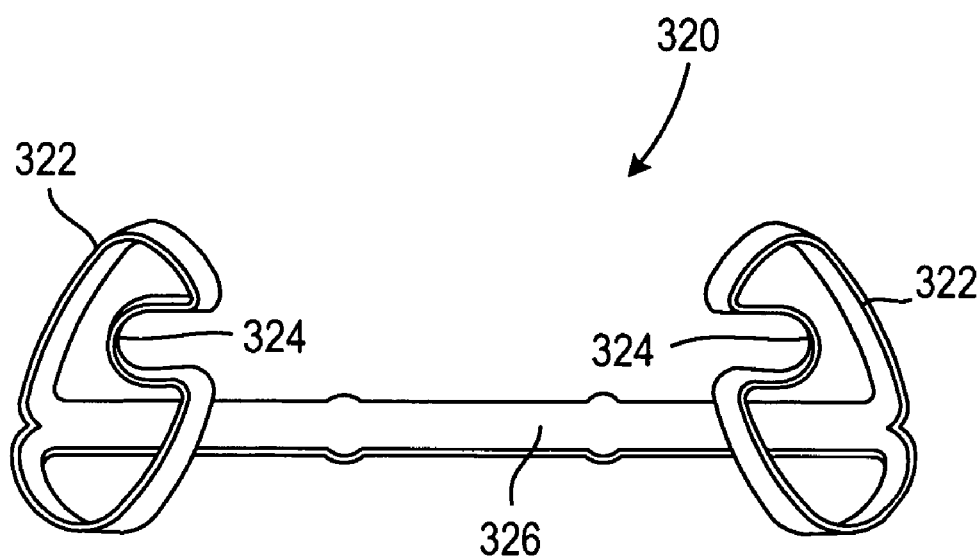
FIG. 25 is a perspective view of an incision structure in accordance with the present invention.

An example of such a structure in accordance with the present invention is incision structure 320, as shown in perspective view in FIG. 25. As shown, incision structure 320 includes end portions 322 that each have an incision member 324 for holding open an incision in a target vessel. Member 326 may connect end portions 322 to one another.

Figure 26:
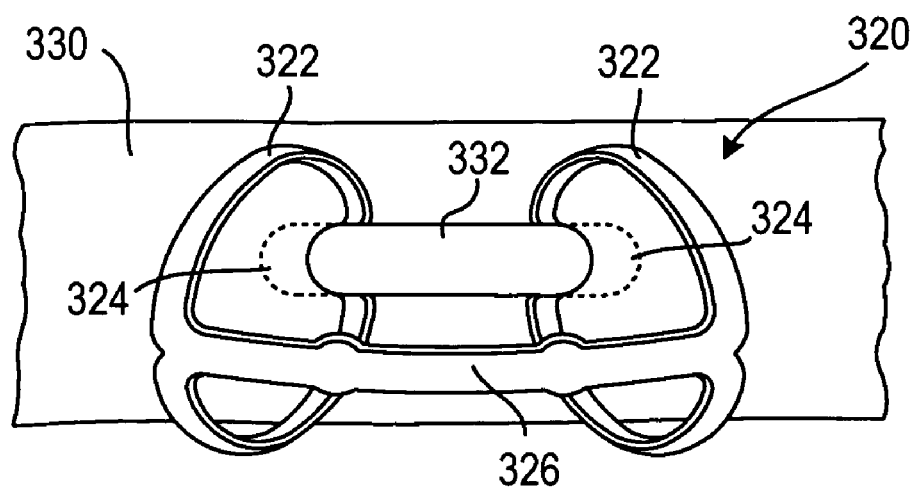
FIG. 26 is a perspective view illustrating the incision structure of FIG. 25 installed in an incision in accordance with the present invention.

As shown in FIG. 26, incision structure 320 may be inserted into an incision 332 in a target vessel 330 by compressing end portions 322 toward one another, such that both incision members 324 enter the incision. (Incision members 324 are represented in FIG. 26 by dashed lines, showing the orientation of the incision members beneath the surface of target vessel 330.)

Figure 27:
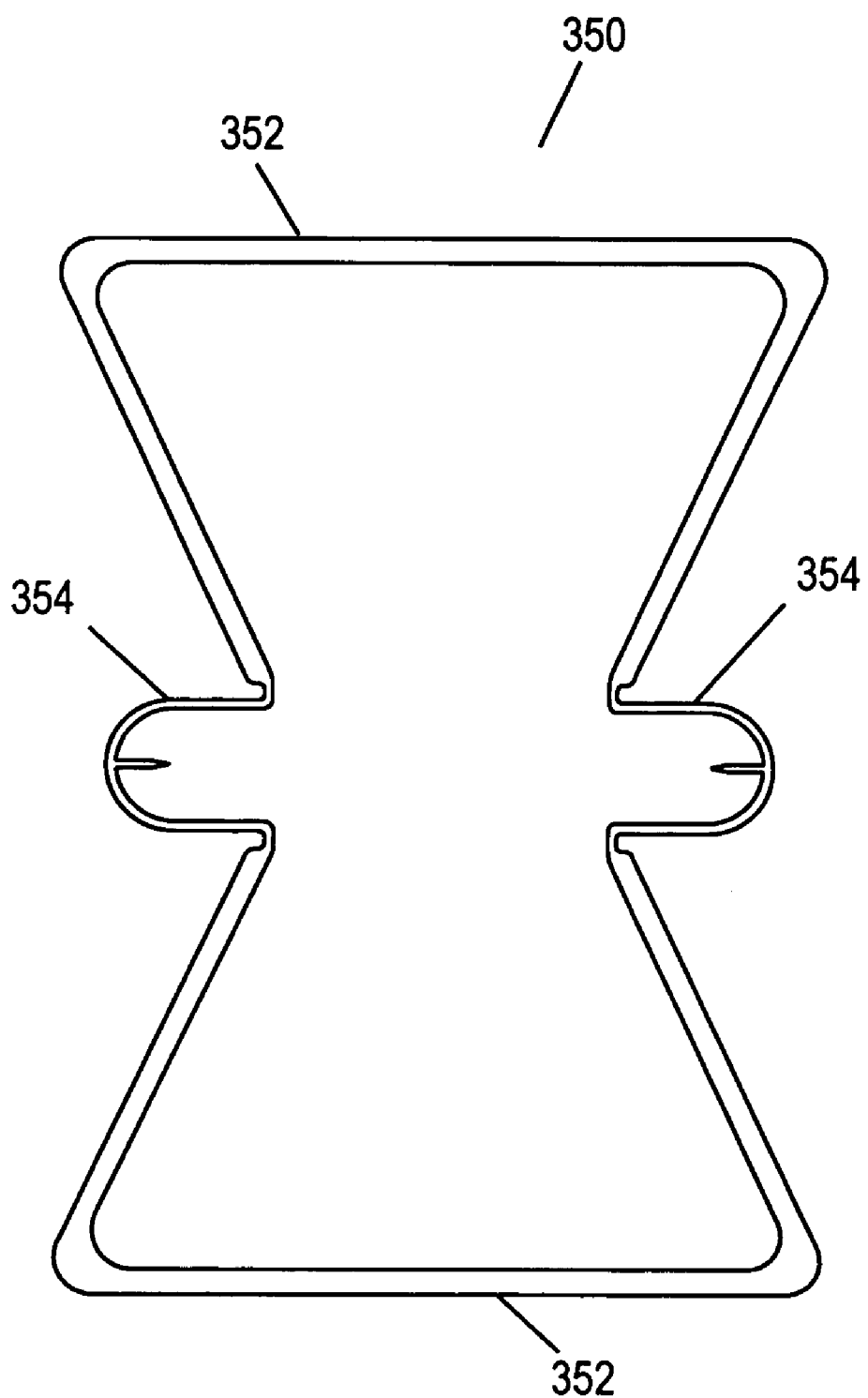
FIG. 27 is a perspective view of another incision structure in accordance with the present invention.

Another example of a structure for insertion into an incision in a target vessel in accordance with the present invention is incision structure 350, shown in FIG. 27. As shown, incision structure 350 includes end portions 352 that each have an incision member 354 for holding open an incision in a target vessel. Incision structure 350 may be inserted into an incision in a target vessel (see, for example, incision 332 of FIG. 26) by compressing each end portion 352 "closed." In other words, each end portion 352 may be compressed at some location close to where the end portions attach to incision members 354, such that incision members 354 approach one another. By doing so, both incision embers 354 may enter the incision (see, for example, incision 332 of FIG. 26).

In accordance with the present invention, an assembly that includes a graft conduit and a graft connector may be attached to the target vessel connector. The graft connector may include graft attachment hooks and target vessel attachment hooks. These hooks may be shielded when the graft connector and a delivery device (see, for example, FIGS. 13-19) are loaded into an incision in the side wall of the graft conduit via a severed end of the graft conduit. The incision in the side wall of the graft conduit may be made, for example, as described hereinabove in connection with FIGS. 2-5. Alternatively, the incision in the graft conduit may be made using any other suitable technique, such as that described in published PCT patent publication No. WO 01/39672, published Jun. 7, 2001, which is incorporated by reference hereinabove. Once the graft connector is loaded into the incision in the graft conduit, the shield may be removed, and the graft-connector assembly is ready to be coupled to the target vessel connector.

The graft connector of the present invention may be plastically deformable. The structure of the graft connector may have a specified perimeter for insertion into the incision, and a specified perimeter for expansion within the incision. As described hereinabove in connection with the various illustrative target vessel connectors, the graft connector may have the same "shortening" feature, resulting in a shortening of the distance between graft attachment hooks and target vessel attachment hooks.

A delivery device such as the delivery device described hereinabove in connection with FIGS. 13-19 may be used to deliver and install a graft-connector assembly in an incision in a target vessel. The delivery device may include a nosecone, a shield, a shoehorn, any other suitable device, or combination of such devices to prevent graft attachment hooks from damaging the tissue of the graft conduit. The means for shielding the graft attachment hooks may be removed once the graft conduit is loaded onto the graft connector. Alternatively, the means for shielding the graft attachment hooks may remain in place during loading and delivery of the graft connector. The shielding of the graft attachment hooks may be either static (e.g., part of the anvil structures of the delivery device), or dynamic (e.g., moving out of the way once the expansion of the graft connector is complete).

Figure 28:
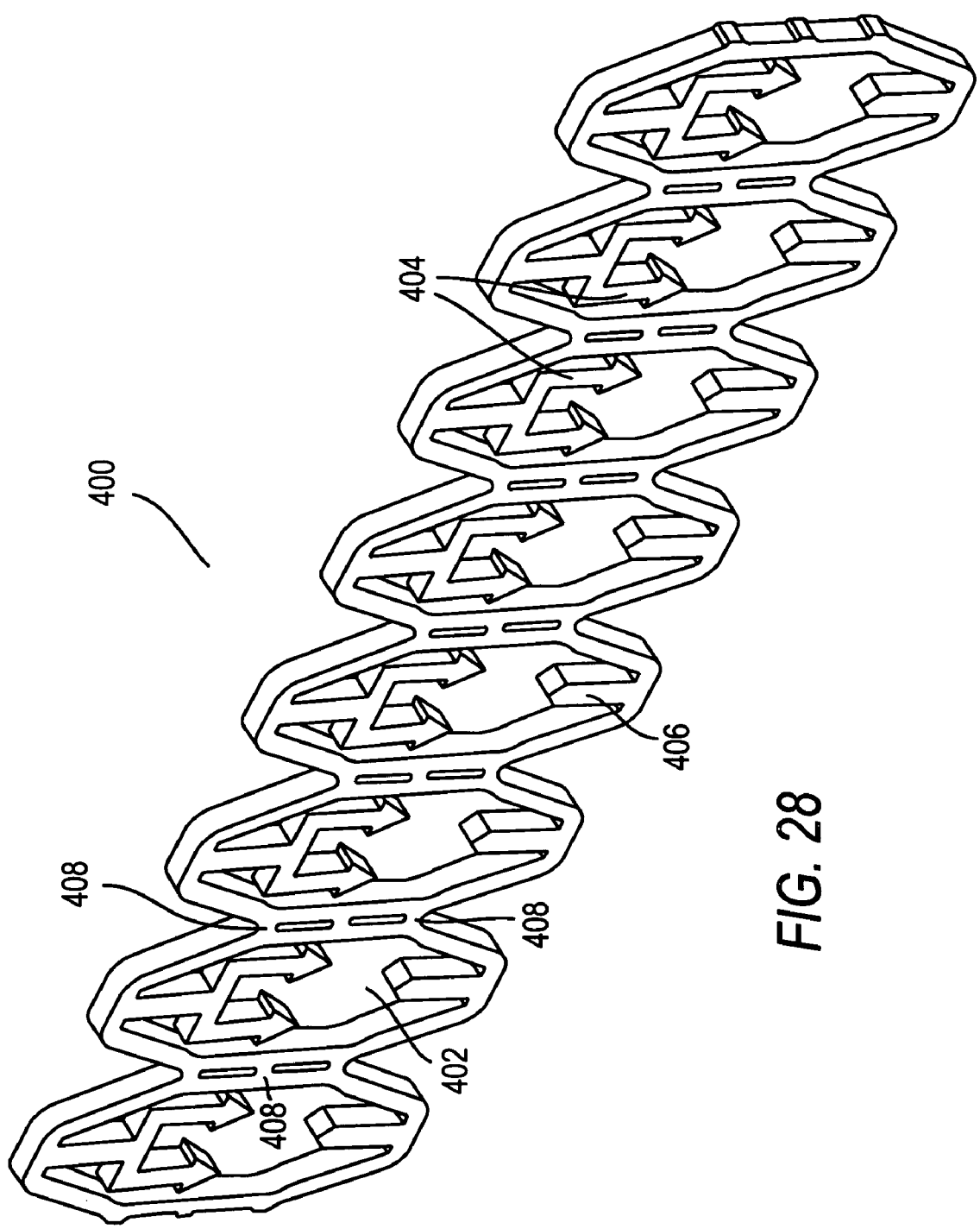
FIG. 28 is a planar development of a graft connector structure in accordance with the present invention.
Figure 29:
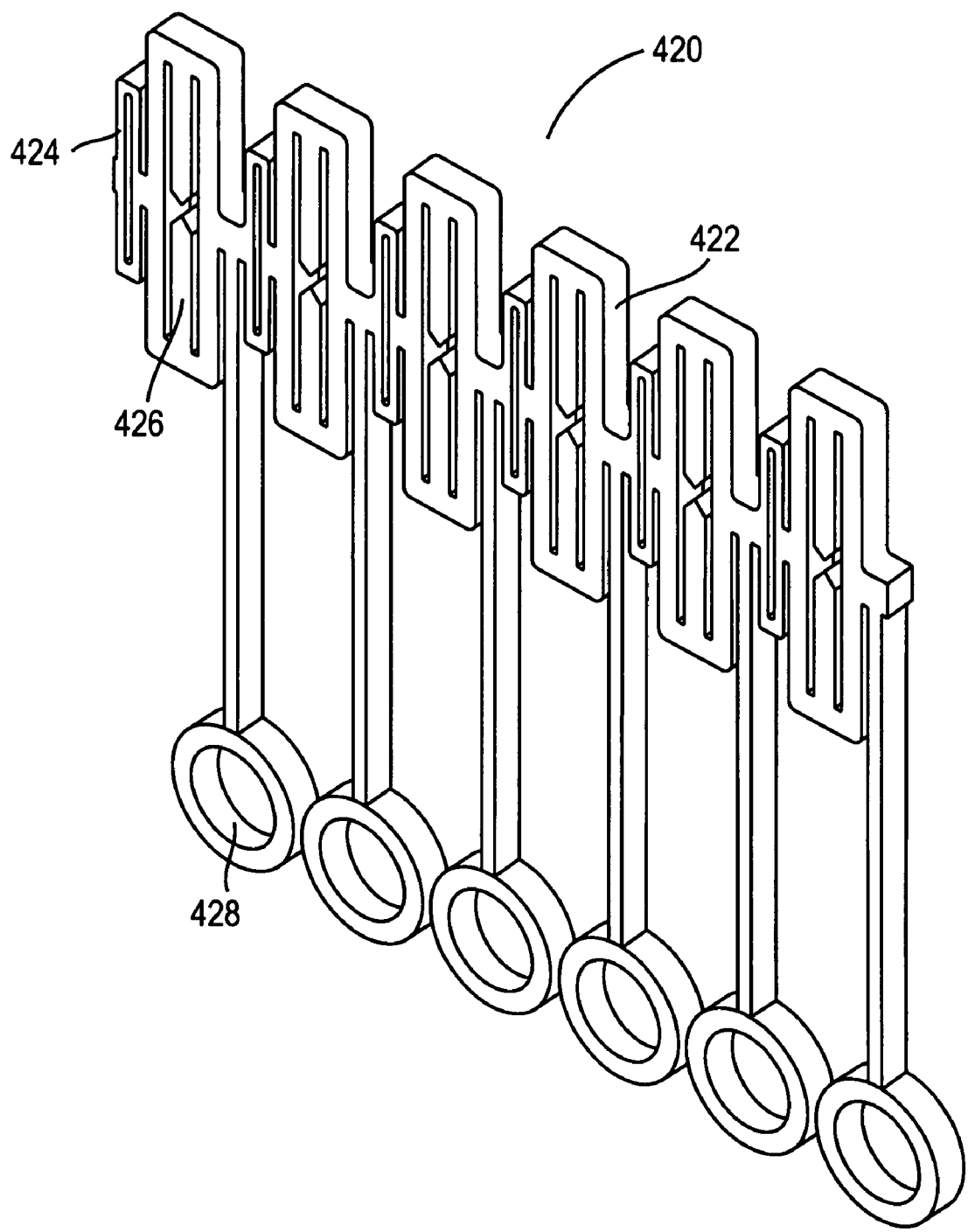
FIG. 29 is a planar development of another graft connector structure in accordance with the present invention.

Embodiments of a graft connector in accordance with the present invention are now described in connection with FIGS. 28 and 29. The connectors in FIGS. 28 and 29 (shown in planar development) are suitable for coupling to a graft conduit for installation in an incision in a target vessel. In some embodiments of the present invention, a target vessel connector may be installed within the incision in the target vessel. The connectors of FIGS. 28 and 29 are of a similar size as target vessel connector 100 (FIGS. 8 and 9), and the graft connectors are constructed of the same material or materials as target vessel connector 100. (It should be noted, however, that the graft connectors of FIGS. 28 and 29 may be slightly larger than connector 100 and the other illustrative target vessel connectors since the graft connectors may encapsulate the target vessel connector when installed in the target vessel incision.) The differences between the embodiments of graft connectors shown in FIGS. 28 and 29 and target vessel connector 100 are made apparent in the description that follows.

An illustrative embodiment of a connector 400 in accordance with the present invention is shown in FIG. 28. The distance between graft members 404 and target vessel members 406 of cells 402 is greater than distance 114 of connector 100 (i.e., the equivalent distance for connector 100). This difference in size is due to the fact that connector 400 accommodates two layers of tissue (i.e., the target vessel tissue and the graft conduit tissue), rather than just one layer of tissue as with connector 100 (i.e., the target vessel tissue). Connector 400 may have additional barbed members 404 for engaging the inner surface of the graft conduit. Cells 402 of connector 400 may be connected to adjoining cells at multiple locations 408 for each cell. Connecting cells 402 at multiple locations 408 results in a stable cell configuration in which adjacent cells resist twisting with respect to one another.

Another illustrative embodiment of a graft connector 420 in accordance with the present invention is shown in FIG. 29. In addition to cells 422, connector 420 also has additional cells 424. Cells 424 have a smaller wall thickness than cells 422. Because of the difference in wall thickness, cells 424 may expand prior to cells 422 when connector 400 is expanded (e.g., using a suitable delivery device). his allows the perimeter of the incision to become taut against connector 400 before larger cells 422 foreshorten. Thus, smaller cells 424 aid in positioning connector 400 properly within the target vessel incision.

In addition to members 426, connector 420 also includes looped members 428. In some embodiments of the present invention, looped members may reside within the target vessel after deployment of graft connector 420. Alternatively, looped members 428 may reside on the outer surface of the target vessel, and may be joined to certain members of the target vessel connector by, for example, lacing a suture between looped members 428 and the members of the target vessel connector. For example, referring to FIG. 11, connector 140 has looped members 148 which may be joined to looped members 428 of connector 420. In such embodiments, it may be unnecessary to use a delivery device to deploy graft connector 420.

FIGS. 30-37 illustrate a method for attaching a graft connector and graft conduit assembly to a target vessel connector using, for example, delivery device 170 of FIGS. 13 and 14 in accordance with the present invention. One or both of the graft conduit and target vessel may have a small diameter.

A connector such as connector 400 (FIG. 28) may be disposed annularly around elongated members 181 and 183 of delivery device 170. For simplicity, a simplified version of connector 400 (FIG. 28) is shown in FIG. 30. (It should be noted that the use of connector structure 400 is merely illustrative, and any suitable connector structure may be used along with a graft conduit for attachment to a target vessel.)

Delivery device 170 may enter graft 450 through a severed end 456. The distal end of delivery device 170, and in particular anvil structures 180 and 182, may be shielded during the introduction into graft 450 to prevent target vessel members 406 from snagging on the tissue of the graft. For example, a shield (not shown) may be provided that is annularly disposed around sheath portion 174. Alternatively, anvil 180 may prevent members 406 from snagging on the tissue of graft 450.

An incision 454 may be made in side wall 452 of graft 450 in a manner such as that described hereinabove in connection with FIGS. 2-5. Alternatively, incision 454 may be made in vessel 450 using any other suitable technique, such as that described in PCT patent publication No. WO 01/39672, published Jun. 7, 2001, which is incorporated by reference hereinabove. Anvil structure 182 may be inserted into incision 454 at some angle to prevent snagging side wall 452 on target vessel members 406 (see FIG. 31). Anvil structure 180 may then be inserted into incision 454, attaining the configuration shown in FIG. 32. It should be noted that, while the example illustrated in FIGS. 31 and 32 shows anvil structure 182 entering incision 454 prior to anvil structure 180, this is merely illustrative. Either anvil structure 180 or anvil structure 182 may enter incision 454 prior to the other anvil structure.

Once connector 400 has been encapsulated within incision 454, the assembly of connector 400 and graft 450 may be attached to target vessel 300 (FIG. 33). In particular, the assembly of connector 400 and graft 450 may be attached to target vessel connector 100. Target vessel connector 100 may be installed in target vessel 300 as described hereinabove in connection with FIGS. 20-24. Anvil structure 180 may be inserted into incision 304 at some angle, followed by anvil structure 180, thereby attaining the configuration shown in FIG. 34. Again, while the example illustrated in FIGS. 33 and 34 shows anvil structure 180 entering incision 304 prior to anvil structure 182, this is merely illustrative, and either anvil structure may enter incision 454 prior to the other anvil structure.

After connector 400 has been encapsulated within both incisions 454 and 304, as shown in FIG. 34, the connector may be expanded such that graft members 404 engage graft side wall 452, and target vessel members 406 engage target vessel side wall 302. To expand connector 400 in the axial direction of target vessel 300, handle portion 172 of delivery device may be pulled in direction 184 (FIG. 13), resulting in the configuration shown in FIG. 35. To expand connector 400 in the radial direction of target vessel 300, handle portion 172 of delivery device 170 may be rotated in direction 176 (FIG. 13), resulting in the configuration shown in FIG. 36. Delivery device 170 may then be removed through severed end 456, and the severed end may be tied of with, for example, a ligature 458 (see FIG. 37). This leaves side wall 452 of graft conduit 450 connected to side wall 302 of target vessel 300 by enlarged connector 400. (It will be appreciated that FIG. 37 is greatly simplified in that it only shows the portion of connectors 100 and 400 and the anastomosis that are in the plane of the page on which FIG. 37 is drawn. Connectors 100 and 400 and the resulting anastomosis are in fact fully annular, all the way around communicating apertures 454 and 304 in side walls 452 and 302, respectively.) In some embodiments of the present invention, connector 400 may be expanded in the axial direction of target vessel 300 more than it is expanded in the radial direction of the target vessel. This difference in expansion results in a non-round (e.g., oval) expanded connector 400.

By expanding connector 400 in both the axial and radial directions of target vessel 300, graft members 404 and target vessel members 406 engage side wall 452 of graft 450 and side wall 302 of target vessel 300, respectively. Preferably, both graft members 404 and target vessel members 406 penetrate the inner surfaces of side walls 452 and 302, respectively. In particular, graft members 404 preferably penetrate the inner surface of side wall 452 around the periphery of incision 454, and target vessel members 406 preferably penetrate the inner surface of side wall 302 around the periphery of incision 304. Alternatively, one or both of graft members 404 and target vessel members 406 may engage, but not penetrate, the inner surfaces of side walls 452 and 302, respectively.

Anvil structures 180 and 182, and any of the other anvil structures described herein in connection with other embodiments of the delivery device of the present invention, may be of any suitable shape in order to achieve the desired expanded configuration of connector 400.

It should be noted that, while the example of FIGS. 30-37 is shown using delivery device 170, this is merely illustrative, and any suitable delivery device may be used to attach an assembly of a graft connector and a graft conduit to a target vessel connector. For example, any of the delivery devices shown in FIGS. 15-19 may be used to install the graft connector and graft conduit assembly.

As described hereinabove in connection with FIGS. 30-37, a graft connector may be attached to a target vessel connector such that the graft connector encapsulates the target vessel connector. Alternatively, the graft connector and target vessel connector may be positioned adjacent to one another. An illustrative example of such an embodiment is shown in FIG. 38. As shown in FIG. 38, two connectors 500 are provided that are similar to connector 100 (as shown in FIGS. 8 and 9). Each connector 500 may include a plurality of cells 502 and members 504 for engaging tissue, such as that of a graft conduit or a target vessel. One connector 500 may be positioned adjacent to the other connector 500, such that the cell structure of one connector 500 "meshes" with the cell structure of the other connector 500.

In some embodiments of the present invention, a target vessel connector that holds open an incision in a target vessel (see, for example, FIGS. 8-12) may be eliminated. A graft connector may be introduced directly into the target vessel, after having loaded the graft conduit onto the graft connector, without the aid of the target vessel connector holding open the target vessel incision.

It will be understood that the foregoing is only illustrative of the principles of the invention, and that still other modifications can be made by those skilled in the art without departing from the scope and spirit of the invention. For example, the various materials and dimensions mentioned herein are only examples, and other materials and dimensions can be used, if desired.

What is claimed is:

1. Apparatus for creating an incision having a controlled length in a side wall of a patient's body tissue conduit, comprising:
    a tip portion having a sharpened free end portion, wherein the tip portion is configured for insertion into the side wall of the body tissue conduit such that the sharpened free end portion creates a first hole in the side wall and a second hole in the side wall at some distance from the first hole; and
    a blade portion attached to the tip portion, wherein an angle between the blade portion and the tip portion is less than 180°, and wherein the blade portion is configured to create an incision between the first and second holes, wherein the tip portion has a recessed portion that is configured to indicate a proper insertion depth of the tip portion into the side wall of the body tissue conduit.

2. The apparatus defined in claim 1, further comprising: a handle portion attached to the blade portion.

3. The apparatus defined in claim 1, further comprising: a handle portion attached to the blade portion, wherein an angle between the handle portion and the blade portion is less than 180°.

4. The apparatus defined in claim 1, wherein a cross section of the tip portion increases in size from the sharpened free end portion of the tip portion.

5. The apparatus defined in claim 1, wherein the tip portion is substantially straight between the sharpened free end portion and the recessed portion, and wherein the incision has a length that is approximately equal to a length of the tip portion between the sharpened free end portion and the recessed portion.

6. The apparatus defined in claim 1, wherein the tip portion is curved between the sharpened free end portion and the recessed portion, and wherein the incision has a length that is approximately equal to a chord length extending between the sharpened free end portion and the recessed portion.

7. A method for creating an incision having a controlled length in a side wall of a patient's body tissue conduit, comprising:
    providing an incision tool comprising:
        a tip portion having a sharpened free end portion; and
        a blade portion attached to the tip portion, wherein an angle between the blade portion and the tip portion is less than 180°;
    creating a first hole in the side wall of the body tissue conduit with the sharpened free end portion;
    creating a second hole in the side wall of the body tissue conduit with the sharpened free end portion; and
    cutting from the first hole to the second hole with the blade portion such that an incision is created, wherein the tip portion has a recessed portion that is configured to indicate a proper insertion depth of the tip portion into the side wall of the body tissue conduit, the method further comprising:
    after creating the first hole in the side wall, advancing the tip portion into the body tissue conduit until the recessed portion is encapsulated by the side wall.

8. The method defined in claim 7, wherein the creating the first hole in the side wall of the body tissue conduit further comprises:
    inserting the sharpened free end portion of the tip portion into the side wall of the body tissue conduit such that the first hole is created in the side wall.

9. The method defined in claim 7, wherein the creating the second hole in the side wall of the body tissue conduit further comprises:
    rotating the incision tool such that the sharpened free end portion of the tip portion emerges from within the body tissue conduit and the second hole is created in the side wall.

10. The method defined in claim 7, wherein the cutting from the first hole to the second hole with the blade portion further comprises:
    rotating the incision tool.

11. A method for inserting a hollow annular connector into an aperture in a side wall of a patient's body tissue conduit, comprising:
    providing a delivery device comprising:
        a first anvil structure, wherein the first anvil structure is attached to a first movable member such that the first movable member effects the movement of the first anvil structure; and
        a second anvil structure, wherein the first and second anvil structures are disposed at least partially within the hollow annular connector;
    introducing the hollow annular connector into the aperture;

advancing the first anvil structure away from the second anvil structure along the axis of the body tissue conduit such that the connector expands in the axial direction of the body tissue conduit; and advancing the first anvil structure away from the second anvil structure perpendicular to the axis of the body tissue conduit such that the connector expands in the radial direction of the body tissue conduit.

12. The method of claim 11, wherein the advancing the first anvil structure away from the second anvil structure along the axis of the body tissue conduit further comprises advancing the first anvil structure an axial distance, wherein the advancing the first anvil structure away from the second anvil structure perpendicular to the axis of the body tissue conduit comprises advancing the first anvil structure a radial distance, and wherein the axial distance is greater than the radial distance such that the connector achieves a non-round configuration.

13. A method for inserting a hollow annular connector into an aperture in a side wall of a body tissue conduit, comprising:

providing a delivery device comprising:
an expansion structure; and
a movable member attached to the expansion structure, wherein the movable member effects the movement of the expansion structure;

disposing the connector around a portion of the delivery device;

introducing the connector into the aperture; and moving the expansion structure such that the connector expands in the axial direction of the body tissue conduit and in the radial direction of the body tissue conduit, and wherein the expansion in the axial direction of the body tissue conduit is greater than the expansion in the radial direction of the body tissue conduit such that the connector achieves a non-round configuration.

* * * * *